(12) United States Patent
Stalcup et al.

(10) Patent No.: US 9,358,056 B2
(45) Date of Patent: Jun. 7, 2016

(54) ORTHOPAEDIC IMPLANT

(75) Inventors: Gregory C. Stalcup, Columbia City, IN (US); Sarah L. Zimmerman, Columbia City, IN (US); Paul S. Nebosky, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 500 days.

(21) Appl. No.: 12/549,996

(22) Filed: Aug. 28, 2009

(65) Prior Publication Data

US 2010/0042215 A1    Feb. 18, 2010

Related U.S. Application Data

(63) Continuation-in-part of application No. 12/540,760, filed on Aug. 13, 2009, now Pat. No. 8,475,505.

(60) Provisional application No. 61/092,890, filed on Aug. 29, 2008, provisional application No. 61/088,383, filed on Aug. 13, 2008.

(51) Int. Cl.
| | |
|---|---|
| *A61B 17/86* | (2006.01) |
| *A61B 17/68* | (2006.01) |
| *A61B 17/70* | (2006.01) |
| *A61B 17/80* | (2006.01) |
| *A61B 17/58* | (2006.01) |
| *A61B 17/88* | (2006.01) |

(52) U.S. Cl.
CPC .............. *A61B 17/864* (2013.01); *A61B 17/68* (2013.01); *A61B 17/7098* (2013.01); *A61B 17/8095* (2013.01); *A61B 17/866* (2013.01); *A61B 17/58* (2013.01); *A61B 17/86* (2013.01); *A61B 17/8685* (2013.01); *A61B 17/8802* (2013.01)

(58) Field of Classification Search
None
See application file for complete search history.

(56) References Cited

U.S. PATENT DOCUMENTS

| | | |
|---|---|---|
| 3,662,405 A | 5/1972 | Bortz et al. |
| 3,683,421 A | 8/1972 | Martinie |
| 3,855,638 A | 12/1974 | Pilliar |
| 3,867,728 A | 2/1975 | Stubstad et al. |
| 4,011,602 A | 3/1977 | Rybicki et al. |
| 4,060,081 A | 11/1977 | Yannas et al. |
| 4,156,943 A | 6/1979 | Collier |
| 4,222,128 A | 9/1980 | Tomonaga et al. |

(Continued)

FOREIGN PATENT DOCUMENTS

| | | |
|---|---|---|
| DE | 4211345 C1 | 11/1993 |
| DE | 4423020 A1 | 1/1996 |

(Continued)

OTHER PUBLICATIONS

Office Action dated Jan. 5, 2010 in U.S. Appl. No. 11/060,377 (10 pages).

(Continued)

*Primary Examiner* — Yashita Sharma
*Assistant Examiner* — Rebecca Preston
(74) *Attorney, Agent, or Firm* — Taylor IP, P.C.

(57) ABSTRACT

An orthopaedic implant system includes an orthopaedic implant implantable at a selected location within a corporeal body. The implant includes a first structural material and a second structural material. The first structural material is non-resorbable relative to the corporeal body and is different relative to the second structural material. The implant is an internal fixation device.

20 Claims, 10 Drawing Sheets

(56) References Cited

U.S. PATENT DOCUMENTS

| | | |
|---|---|---|
| 4,450,150 A | 5/1984 | Sidman |
| 4,453,537 A | 6/1984 | Spitzer |
| 4,485,097 A | 11/1984 | Bell |
| 4,520,821 A | 6/1985 | Schmidt et al. |
| 4,608,052 A | 8/1986 | Van Kampen et al. |
| 4,609,551 A | 9/1986 | Caplan et al. |
| 4,620,327 A | 11/1986 | Caplan et al. |
| 4,644,627 A | 2/1987 | Palazzo |
| 4,660,755 A | 4/1987 | Farling et al. |
| 4,737,411 A | 4/1988 | Graves, Jr. et al. |
| 4,769,041 A | 9/1988 | Morscher |
| 4,846,834 A | 7/1989 | Von Recum et al. |
| 4,858,603 A | 8/1989 | Clemow et al. |
| 4,936,859 A | 6/1990 | Morscher et al. |
| 4,976,738 A | 12/1990 | Frey et al. |
| 5,030,233 A | 7/1991 | Ducheyne |
| 5,041,107 A | 8/1991 | Heil, Jr. |
| 5,084,051 A | 1/1992 | Tormala et al. |
| 5,092,898 A | 3/1992 | Bekki et al. |
| 5,100,392 A | 3/1992 | Orth et al. |
| 5,104,410 A | 4/1992 | Chowdhary |
| 5,190,550 A | 3/1993 | Miller et al. |
| 5,197,985 A | 3/1993 | Caplan et al. |
| 5,204,055 A | 4/1993 | Sachs et al. |
| 5,219,363 A | 6/1993 | Crowninshield et al. |
| 5,226,914 A | 7/1993 | Caplan et al. |
| 5,281,210 A | 1/1994 | Burke et al. |
| 5,282,861 A | 2/1994 | Kaplan |
| 5,306,309 A | 4/1994 | Wagner et al. |
| 5,328,765 A | 7/1994 | Anderson et al. |
| 5,370,690 A | 12/1994 | Barrett |
| 5,380,328 A | 1/1995 | Morgan |
| 5,443,471 A | 8/1995 | Swajger |
| 5,458,643 A | 10/1995 | Oka et al. |
| 5,462,362 A | 10/1995 | Yuhta et al. |
| 5,490,962 A | 2/1996 | Cima et al. |
| 5,496,372 A | 3/1996 | Hamamoto et al. |
| 5,514,182 A | 5/1996 | Shea |
| 5,518,680 A | 5/1996 | Cima et al. |
| 5,531,750 A | 7/1996 | Even-Esh |
| 5,534,028 A | 7/1996 | Bao et al. |
| 5,537,851 A | 7/1996 | Sheu et al. |
| 5,549,700 A | 8/1996 | Graham et al. |
| 5,571,187 A | 11/1996 | Devanathan |
| 5,593,443 A | 1/1997 | Carter et al. |
| 5,637,175 A | 6/1997 | Feygin et al. |
| 5,641,323 A | 6/1997 | Caldarise |
| 5,702,449 A | 12/1997 | McKay |
| 5,730,817 A | 3/1998 | Feygin et al. |
| 5,732,469 A | 3/1998 | Hamamoto et al. |
| 5,750,103 A | 5/1998 | Cherksey |
| 5,769,897 A | 6/1998 | Harle |
| 5,776,199 A | 7/1998 | Michelson |
| 5,800,828 A | 9/1998 | Dionne et al. |
| 5,807,406 A | 9/1998 | Brauker et al. |
| 5,848,989 A | 12/1998 | Villani |
| 5,849,015 A | 12/1998 | Haywood et al. |
| 5,869,170 A | 2/1999 | Cima et al. |
| 5,871,484 A | 2/1999 | Spievack et al. |
| 5,876,550 A | 3/1999 | Feygin et al. |
| 5,879,406 A | 3/1999 | Lilley |
| 5,916,269 A | 6/1999 | Serbousek et al. |
| 5,971,985 A | 10/1999 | Carchidi et al. |
| 5,989,250 A | 11/1999 | Wagner et al. |
| 6,010,336 A | 1/2000 | Shimotoso et al. |
| 6,045,581 A | 4/2000 | Burkinshaw |
| 6,110,179 A | 8/2000 | Flivik et al. |
| 6,136,029 A | 10/2000 | Johnson et al. |
| 6,136,031 A | 10/2000 | Middleton |
| 6,139,574 A | 10/2000 | Vacanti et al. |
| 6,143,035 A | 11/2000 | McDowell |
| 6,159,247 A | 12/2000 | Klawitter et al. |
| 6,176,874 B1 | 1/2001 | Vacanti et al. |
| 6,238,435 B1 | 5/2001 | Meulink et al. |
| 6,283,997 B1 | 9/2001 | Garg et al. |
| 6,290,726 B1 | 9/2001 | Pope et al. |
| 6,306,424 B1 | 10/2001 | Vyakarnam et al. |
| 6,315,797 B1 | 11/2001 | Middleton |
| 6,322,564 B1 | 11/2001 | Surma |
| 6,328,765 B1 | 12/2001 | Hardwick et al. |
| 6,333,029 B1 | 12/2001 | Vyakarnam et al. |
| 6,337,198 B1 | 1/2002 | Levene et al. |
| 6,365,149 B2 | 4/2002 | Vyakarnam et al. |
| 6,379,391 B1 | 4/2002 | Masini |
| 6,395,011 B1 | 5/2002 | Johanson et al. |
| 6,409,764 B1 | 6/2002 | White et al. |
| 6,419,704 B1 | 7/2002 | Ferree |
| 6,423,095 B1 | 7/2002 | Van Hoeck et al. |
| 6,423,252 B1 | 7/2002 | Chun et al. |
| 6,425,921 B1 | 7/2002 | Grundei et al. |
| 6,440,734 B1 | 8/2002 | Pykett et al. |
| 6,454,811 B1 | 9/2002 | Sherwood et al. |
| 6,461,385 B1 | 10/2002 | Gayer et al. |
| 6,471,689 B1 | 10/2002 | Joseph et al. |
| 6,471,993 B1 | 10/2002 | Shastri et al. |
| 6,475,137 B1 | 11/2002 | Elist |
| 6,494,916 B1 | 12/2002 | Babalola et al. |
| 6,514,514 B1 | 2/2003 | Atkinson et al. |
| 6,520,993 B2 | 2/2003 | James et al. |
| 6,526,984 B1 | 3/2003 | Nilsson et al. |
| 6,527,810 B2 | 3/2003 | Johnson et al. |
| 6,530,958 B1 | 3/2003 | Cima et al. |
| 6,533,818 B1 | 3/2003 | Weber et al. |
| 6,534,084 B1 | 3/2003 | Vyakarnam et al. |
| 6,544,472 B1 | 4/2003 | Compton et al. |
| 6,547,824 B1 | 4/2003 | Price |
| 6,551,290 B1 | 4/2003 | Elsberry et al. |
| 6,554,857 B1 | 4/2003 | Zilla et al. |
| 6,565,572 B2 | 5/2003 | Chappius |
| 6,571,130 B1 | 5/2003 | Ljungstrom et al. |
| 6,599,322 B1 | 7/2003 | Amrich et al. |
| 6,610,095 B1 | 8/2003 | Pope et al. |
| 6,626,950 B2 | 9/2003 | Brown et al. |
| 6,635,049 B1 | 10/2003 | Robinson et al. |
| 6,645,251 B2 | 11/2003 | Salehi et al. |
| 6,656,489 B1 | 12/2003 | Mahmood et al. |
| 6,660,040 B2 | 12/2003 | Chan et al. |
| 6,673,108 B2 | 1/2004 | Zilla et al. |
| 6,682,567 B1 | 1/2004 | Schroeder |
| 6,692,528 B2 | 2/2004 | Ward et al. |
| 6,709,463 B1 | 3/2004 | Pope et al. |
| 6,709,464 B2 | 3/2004 | Scott et al. |
| 6,712,850 B2 | 3/2004 | Vyakarnam et al. |
| 6,723,120 B2 | 4/2004 | Yan |
| 6,736,850 B2 | 5/2004 | Davis |
| 6,749,636 B2 | 6/2004 | Michelson |
| 6,758,863 B2 | 7/2004 | Estes et al. |
| 6,783,546 B2 | 8/2004 | Zucherman et al. |
| 6,818,620 B2 | 11/2004 | Bhatnagar |
| 6,852,272 B2 | 2/2005 | Artz et al. |
| 6,863,899 B2 | 3/2005 | Koblish et al. |
| 6,866,685 B2 | 3/2005 | Chan et al. |
| 6,881,413 B1 | 4/2005 | Bartholeyns |
| 6,893,465 B2 | 5/2005 | Huang |
| 6,913,623 B1 | 7/2005 | Zhu |
| 6,916,321 B2 | 7/2005 | TenHuisen et al. |
| 6,958,078 B2 | 10/2005 | Goel et al. |
| 6,969,383 B2 | 11/2005 | Hildebrand |
| 6,979,353 B2 | 12/2005 | Bresina |
| 6,989,033 B1 | 1/2006 | Schmidt |
| 6,993,406 B1 | 1/2006 | Cesarano, III et al. |
| 7,018,416 B2 | 3/2006 | Hanson et al. |
| 7,018,418 B2 | 3/2006 | Amrich et al. |
| 7,052,710 B2 | 5/2006 | Giordano et al. |
| 7,077,867 B1 | 7/2006 | Pope et al. |
| 7,087,086 B2 | 8/2006 | Li et al. |
| 7,087,200 B2 | 8/2006 | Taboas et al. |
| 7,090,668 B1 | 8/2006 | U et al. |
| 7,094,371 B2 | 8/2006 | Lo |
| 7,108,828 B2 | 9/2006 | Lefebvre et al. |
| 7,112,223 B2 | 9/2006 | Davis |
| 7,128,762 B2 | 10/2006 | Middleton |
| 7,174,282 B2 | 2/2007 | Hollister et al. |
| 7,189,409 B2 | 3/2007 | Pirhonen et al. |

(56) References Cited

U.S. PATENT DOCUMENTS

| | | |
|---|---|---|
| 7,192,440 B2 | 3/2007 | Andreas et al. |
| 7,208,222 B2 | 4/2007 | Rolfe et al. |
| 7,226,612 B2 | 6/2007 | Sohier et al. |
| 7,238,186 B2 | 7/2007 | Zdeblick et al. |
| 7,238,363 B2 | 7/2007 | Mansouri et al. |
| 7,250,055 B1 | 7/2007 | Vanderwalle |
| 7,250,060 B2 | 7/2007 | Trieu |
| 7,255,713 B2 | 8/2007 | Malek |
| 7,300,439 B2 | 11/2007 | May |
| 7,354,452 B2 | 4/2008 | Foley |
| 7,537,617 B2 | 5/2009 | Bindsell et al. |
| 7,537,664 B2 | 5/2009 | O'Neill et al. |
| 7,575,572 B2 | 8/2009 | Sweeney |
| 7,632,228 B2 | 12/2009 | Brauker et al. |
| 7,632,338 B2 | 12/2009 | Cipollini |
| 7,666,230 B2 | 2/2010 | Orban et al. |
| 7,674,426 B2 | 3/2010 | Grohowski, Jr. |
| 7,674,477 B1 | 3/2010 | Schmid et al. |
| 7,717,956 B2 | 5/2010 | Lang |
| 7,875,080 B2 | 1/2011 | Puno et al. |
| 8,328,555 B2 | 12/2012 | Engman |
| 2001/0038848 A1 | 11/2001 | Donda et al. |
| 2001/0039455 A1 | 11/2001 | Simon et al. |
| 2002/0022884 A1 | 2/2002 | Mansmann |
| 2002/0029083 A1 | 3/2002 | Zucherman et al. |
| 2002/0035400 A1 | 3/2002 | Bryan et al. |
| 2002/0062154 A1 | 5/2002 | Ayers |
| 2002/0072798 A1 | 6/2002 | Riesle et al. |
| 2002/0091447 A1 | 7/2002 | Shimp et al. |
| 2002/0106393 A1 | 8/2002 | Bianchi et al. |
| 2002/0128715 A1 | 9/2002 | Bryan et al. |
| 2002/0143402 A1 | 10/2002 | Steinberg |
| 2002/0161447 A1 | 10/2002 | Salehi et al. |
| 2002/0182241 A1 | 12/2002 | Borenstein et al. |
| 2002/0183850 A1 | 12/2002 | Felt et al. |
| 2002/0197178 A1 | 12/2002 | Yan |
| 2003/0003127 A1 | 1/2003 | Brown et al. |
| 2003/0004578 A1 | 1/2003 | Brown et al. |
| 2003/0006534 A1 | 1/2003 | Taboas et al. |
| 2003/0012805 A1 | 1/2003 | Chen et al. |
| 2003/0023311 A1 | 1/2003 | Trieu |
| 2003/0055506 A1 | 3/2003 | Stoy et al. |
| 2003/0060886 A1 | 3/2003 | Van Hoeck et al. |
| 2003/0060891 A1 | 3/2003 | Shah |
| 2003/0069465 A1 | 4/2003 | Benkowski et al. |
| 2003/0097182 A1 | 5/2003 | Buchman et al. |
| 2003/0105527 A1 | 6/2003 | Bresina |
| 2003/0114934 A1 | 6/2003 | Steinberg |
| 2003/0114936 A1 | 6/2003 | Sherwood et al. |
| 2003/0118649 A1 | 6/2003 | Gao et al. |
| 2003/0120344 A1 | 6/2003 | Michelson |
| 2003/0130743 A1 | 7/2003 | Scott et al. |
| 2003/0139809 A1 | 7/2003 | Worst et al. |
| 2003/0171738 A1 | 9/2003 | Konieczynski et al. |
| 2003/0171820 A1 | 9/2003 | Wilshaw et al. |
| 2003/0180171 A1 | 9/2003 | Artz et al. |
| 2003/0187513 A1 | 10/2003 | Durniak |
| 2003/0203002 A1 | 10/2003 | Murphy et al. |
| 2003/0206928 A1 | 11/2003 | Tormala et al. |
| 2003/0208274 A1 | 11/2003 | Davis |
| 2004/0024400 A1* | 2/2004 | Michelson ......... A61B 17/1671 606/41 |
| 2004/0024470 A1 | 2/2004 | Giordano et al. |
| 2004/0034357 A1 | 2/2004 | Beane et al. |
| 2004/0034427 A1 | 2/2004 | Goel et al. |
| 2004/0063206 A1 | 4/2004 | Rowley et al. |
| 2004/0073197 A1 | 4/2004 | Kim |
| 2004/0115172 A1 | 6/2004 | Bianchi et al. |
| 2004/0126405 A1 | 7/2004 | Sahatjian et al. |
| 2004/0147905 A1 | 7/2004 | Krumme |
| 2004/0153165 A1 | 8/2004 | Li et al. |
| 2004/0158328 A1* | 8/2004 | Eisermann ................ 623/17.16 |
| 2004/0180072 A1 | 9/2004 | Tunc et al. |
| 2004/0191106 A1 | 9/2004 | O'Neill et al. |
| 2004/0191292 A1 | 9/2004 | Chou |
| 2004/0193273 A1 | 9/2004 | Huang |
| 2004/0199260 A1 | 10/2004 | Pope et al. |
| 2004/0210274 A1 | 10/2004 | Bauhahn et al. |
| 2004/0210316 A1 | 10/2004 | King et al. |
| 2004/0215173 A1 | 10/2004 | Kunst |
| 2004/0225360 A1 | 11/2004 | Malone |
| 2004/0249463 A1 | 12/2004 | Bindseil et al. |
| 2004/0265350 A1 | 12/2004 | Sambrook et al. |
| 2004/0267263 A1 | 12/2004 | May |
| 2005/0015059 A1 | 1/2005 | Sweeney |
| 2005/0015150 A1 | 1/2005 | Lee |
| 2005/0021084 A1* | 1/2005 | Lu et al. ................. 606/218 |
| 2005/0049715 A1 | 3/2005 | Ito et al. |
| 2005/0049716 A1 | 3/2005 | Wagener et al. |
| 2005/0055099 A1 | 3/2005 | Ku |
| 2005/0058684 A1 | 3/2005 | Shanley et al. |
| 2005/0059972 A1* | 3/2005 | Biscup ..................... 606/73 |
| 2005/0085888 A1 | 4/2005 | Andreas et al. |
| 2005/0100470 A1 | 5/2005 | Lefebvre et al. |
| 2005/0100578 A1 | 5/2005 | Schmid et al. |
| 2005/0112397 A1 | 5/2005 | Rolfe et al. |
| 2005/0119753 A1 | 6/2005 | McGahan et al. |
| 2005/0125073 A1 | 6/2005 | Orban et al. |
| 2005/0136764 A1* | 6/2005 | Sherman et al. .......... 442/103 |
| 2005/0137707 A1 | 6/2005 | Malek |
| 2005/0143822 A1 | 6/2005 | Paul |
| 2005/0149022 A1* | 7/2005 | Shaolian et al. ........ 606/61 |
| 2005/0159819 A1 | 7/2005 | McCormack et al. |
| 2005/0171611 A1 | 8/2005 | Stoy et al. |
| 2005/0175703 A1 | 8/2005 | Hunter et al. |
| 2005/0177238 A1 | 8/2005 | Khandkar et al. |
| 2005/0177247 A1 | 8/2005 | Canham et al. |
| 2005/0182494 A1 | 8/2005 | Schmid |
| 2005/0187555 A1* | 8/2005 | Biedermann et al. ........... 606/72 |
| 2005/0192669 A1* | 9/2005 | Zdeblick et al. ........... 623/17.11 |
| 2005/0197654 A1 | 9/2005 | Edman et al. |
| 2005/0202371 A1 | 9/2005 | McGuire |
| 2005/0220837 A1 | 10/2005 | Disegi et al. |
| 2005/0222688 A1 | 10/2005 | Zilla et al. |
| 2005/0228503 A1 | 10/2005 | Gundolf |
| 2005/0246032 A1 | 11/2005 | Bokros et al. |
| 2005/0271694 A1 | 12/2005 | Mansouri et al. |
| 2005/0272153 A1 | 12/2005 | Xuenong et al. |
| 2005/0273082 A1 | 12/2005 | Olsen |
| 2005/0273178 A1 | 12/2005 | Boyan et al. |
| 2006/0002810 A1 | 1/2006 | Grohowski, Jr. |
| 2006/0015186 A1 | 1/2006 | Isaac |
| 2006/0047341 A1 | 3/2006 | Trieu |
| 2006/0057737 A1 | 3/2006 | Santini, Jr. et al. |
| 2006/0064170 A1 | 3/2006 | Smith et al. |
| 2006/0064172 A1 | 3/2006 | Trieu |
| 2006/0083730 A1 | 4/2006 | Kusanagi et al. |
| 2006/0093646 A1 | 5/2006 | Cima et al. |
| 2006/0100706 A1 | 5/2006 | Shadduck et al. |
| 2006/0100716 A1 | 5/2006 | Lerf |
| 2006/0105015 A1 | 5/2006 | Perla et al. |
| 2006/0111782 A1 | 5/2006 | Petersen |
| 2006/0111785 A1 | 5/2006 | O'Neil |
| 2006/0121609 A1 | 6/2006 | Yannas et al. |
| 2006/0129242 A1 | 6/2006 | Bergeron et al. |
| 2006/0141012 A1 | 6/2006 | Gingras |
| 2006/0149220 A1 | 7/2006 | Ullestad et al. |
| 2006/0149386 A1 | 7/2006 | Clarke et al. |
| 2006/0173542 A1 | 8/2006 | Shikinami |
| 2006/0178744 A1 | 8/2006 | de Villiers et al. |
| 2006/0193885 A1 | 8/2006 | Leonard Neethling et al. |
| 2006/0195188 A1 | 8/2006 | O'Driscoll et al. |
| 2006/0204581 A1 | 9/2006 | Gower et al. |
| 2006/0229715 A1 | 10/2006 | Istephanous et al. |
| 2006/0235534 A1 | 10/2006 | Gertzman et al. |
| 2006/0241593 A1 | 10/2006 | Sherman et al. |
| 2006/0264950 A1 | 11/2006 | Nelson et al. |
| 2006/0271022 A1 | 11/2006 | Steinbach et al. |
| 2006/0271201 A1 | 11/2006 | Kumar et al. |
| 2006/0276900 A1 | 12/2006 | Carpenter |
| 2006/0282166 A1 | 12/2006 | Molz et al. |
| 2006/0287689 A1 | 12/2006 | Debruyne et al. |
| 2006/0289388 A1 | 12/2006 | Yang et al. |
| 2006/0293757 A1 | 12/2006 | McKay et al. |

(56) References Cited

U.S. PATENT DOCUMENTS

| | | |
|---|---|---|
| 2007/0015110 A1 | 1/2007 | Zhang et al. |
| 2007/0016163 A1 | 1/2007 | Santini, Jr. et al. |
| 2007/0026069 A1 | 2/2007 | Shastri et al. |
| 2007/0038299 A1 | 2/2007 | Stone et al. |
| 2007/0041952 A1 | 2/2007 | Guilak et al. |
| 2007/0043446 A1 | 2/2007 | Murray |
| 2007/0077267 A1 | 4/2007 | Molz, IV et al. |
| 2007/0105222 A1 | 5/2007 | Wolfinbarger et al. |
| 2007/0116734 A1 | 5/2007 | Akash |
| 2007/0123843 A1 | 5/2007 | Gill |
| 2007/0138042 A1 | 6/2007 | Wood |
| 2007/0141105 A1 | 6/2007 | Stein et al. |
| 2007/0141533 A1* | 6/2007 | Ford et al. .................. 433/201.1 |
| 2007/0150063 A1 | 6/2007 | Ruberte et al. |
| 2007/0150064 A1 | 6/2007 | Ruberte et al. |
| 2007/0150068 A1 | 6/2007 | Dong et al. |
| 2007/0160681 A1 | 7/2007 | Park et al. |
| 2007/0161986 A1* | 7/2007 | Levy ............................... 606/61 |
| 2007/0162110 A1 | 7/2007 | Dave |
| 2007/0166348 A1 | 7/2007 | Van Dyke |
| 2007/0168021 A1 | 7/2007 | Holmes, Jr. et al. |
| 2007/0185580 A1 | 8/2007 | Posel |
| 2007/0185585 A1 | 8/2007 | Bracy et al. |
| 2007/0190880 A1 | 8/2007 | Dubrow et al. |
| 2007/0191963 A1 | 8/2007 | Winterbottom et al. |
| 2007/0196419 A1 | 8/2007 | Teller et al. |
| 2007/0202145 A1 | 8/2007 | Ghabrial et al. |
| 2007/0203584 A1 | 8/2007 | Bandyopadhyay et al. |
| 2007/0208420 A1 | 9/2007 | Ameer et al. |
| 2007/0233071 A1* | 10/2007 | Dewey et al. .................. 606/61 |
| 2007/0243225 A1 | 10/2007 | McKay |
| 2007/0250169 A1 | 10/2007 | Lang |
| 2007/0255262 A1 | 11/2007 | Haase |
| 2007/0255416 A1 | 11/2007 | Melkent et al. |
| 2007/0260250 A1* | 11/2007 | Wisnewski et al. ............. 606/73 |
| 2007/0260320 A1 | 11/2007 | Peterman et al. |
| 2007/0270859 A1 | 11/2007 | Companioni et al. |
| 2007/0270974 A1* | 11/2007 | Aeschlimann et al. .... 623/17.19 |
| 2007/0293948 A1 | 12/2007 | Bagga et al. |
| 2008/0004704 A1 | 1/2008 | Katz |
| 2008/0015578 A1 | 1/2008 | Erickson et al. |
| 2008/0046082 A1 | 2/2008 | Lee |
| 2008/0065218 A1 | 3/2008 | O'Neil |
| 2008/0077247 A1 | 3/2008 | Murillo et al. |
| 2008/0109083 A1 | 5/2008 | Van Hoeck et al. |
| 2008/0119945 A1* | 5/2008 | Frigg .......................... 623/23.48 |
| 2008/0147193 A1 | 6/2008 | Matthis et al. |
| 2008/0154314 A1* | 6/2008 | McDevitt ...................... 606/304 |
| 2008/0188940 A1 | 8/2008 | Cohen et al. |
| 2008/0195096 A1* | 8/2008 | Frei .......................... A61B 17/68 606/60 |
| 2008/0200985 A1 | 8/2008 | Robie |
| 2008/0262622 A1 | 10/2008 | Butler |
| 2008/0288074 A1 | 11/2008 | O'Neil et al. |
| 2008/0306609 A1 | 12/2008 | Lee et al. |
| 2009/0005872 A1 | 1/2009 | Moumene et al. |
| 2009/0005874 A1 | 1/2009 | Fleischmann et al. |
| 2009/0024224 A1 | 1/2009 | Chen et al. |
| 2009/0030399 A1 | 1/2009 | Raiszadeh |
| 2009/0132051 A1 | 5/2009 | Moskowitz et al. |
| 2009/0222098 A1 | 9/2009 | Trieu et al. |
| 2009/0228109 A1 | 9/2009 | Pointillant et al. |
| 2009/0248162 A1 | 10/2009 | Peckham |
| 2009/0254182 A1 | 10/2009 | Kovarik et al. |
| 2009/0270986 A1 | 10/2009 | Christensen |
| 2009/0270988 A1 | 10/2009 | Snell et al. |
| 2009/0270991 A1 | 10/2009 | Michelson |
| 2009/0270992 A1 | 10/2009 | Gerber et al. |
| 2009/0276049 A1 | 11/2009 | Weiland |
| 2009/0281517 A1 | 11/2009 | Lambrecht et al. |
| 2009/0281625 A1 | 11/2009 | Enayati |
| 2009/0292363 A1 | 11/2009 | Goldfarb et al. |
| 2009/0326657 A1 | 12/2009 | Grinberg et al. |
| 2010/0003639 A1* | 1/2010 | Salvi et al. .................. 433/174 |
| 2010/0016970 A1 | 1/2010 | Kapitan et al. |
| 2010/0042167 A1 | 2/2010 | Nebosky et al. |
| 2010/0042213 A1 | 2/2010 | Nebosky et al. |
| 2010/0042214 A1 | 2/2010 | Nebosky et al. |
| 2010/0042215 A1 | 2/2010 | Stalcup et al. |
| 2010/0042218 A1 | 2/2010 | Nebosky et al. |
| 2010/0042226 A1 | 2/2010 | Nebosky et al. |
| 2010/0076559 A1 | 3/2010 | Bagga et al. |
| 2010/0174369 A1* | 7/2010 | Wang et al. ................. 623/13.14 |
| 2010/0190254 A1 | 7/2010 | Chian et al. |
| 2010/0234966 A1 | 9/2010 | Lo |
| 2010/0291286 A1 | 11/2010 | O'Neill et al. |
| 2011/0064784 A1 | 3/2011 | Mullens et al. |
| 2011/0153028 A1 | 6/2011 | Albertorio |

FOREIGN PATENT DOCUMENTS

| | | |
|---|---|---|
| DE | 693 28 047 T2 | 3/2000 |
| DE | 19904436 A1 | 8/2000 |
| DE | 10051438 A1 | 5/2002 |
| DE | 695 28 346 T2 | 9/2002 |
| DE | 10120330 A1 | 11/2002 |
| DE | 10157315 C1 | 8/2003 |
| EP | 0617931 A2 | 10/1994 |
| EP | 0827726 A2 | 3/1998 |
| EP | 1 273 312 A2 | 1/2003 |
| EP | 1 287 851 A1 | 3/2003 |
| EP | 1475057 A1 | 11/2004 |
| EP | 1806112 A1 | 7/2007 |
| FR | 2697155 A1 | 4/1994 |
| JP | 6007388 A | 1/1994 |
| JP | 7116184 A | 5/1995 |
| JP | 8173463 A | 7/1996 |
| JP | 2587625 B2 | 12/1996 |
| JP | 2002325781 A | 11/2002 |
| JP | 2005329179 A | 12/2005 |
| WO | 03026714 A1 | 4/2003 |
| WO | 03084602 A2 | 10/2003 |
| WO | 03101504 A1 | 12/2003 |
| WO | 2005/047467 A2 | 5/2005 |
| WO | 2006/088480 A2 | 8/2006 |
| WO | 2006/135727 A2 | 12/2006 |
| WO | 2007/135444 A2 | 11/2007 |

OTHER PUBLICATIONS

Office Action dated Sep. 24, 2010 in U.S. Appl. No. 11/060,377 (7 pages).
A. Cameron, entitled "Basic Lubrication Theory", Ellis Horwood Limited, pp. 134-137, 1976.
A. Cameron, entitled "The Principles of Lubrication", John Wiley and Sons Inc., pp. 542-559, 1966.
Office Action dated May 12, 2010 in U.S. Appl. No. 10/980,425 (22 pages).
Philip E. Mitchell, Handbook Editor, "Tool and Manufacturing Engineers Handbook", 4th Edition, vol. VIII Plastic Part Manufacturing, Society of Manufacturing Engineers, Dearborn, Michigan, pp. 2-17 and 2-18, 1996 (4 pages).
Provisional U.S. Appl. No. 60/149,027, filed Aug. 16, 1999 with U.S. Patent & Trademark Office (44 pages).
U.S. Appl. No. 08/200,636, filed Feb. 23, 1994 with U.S. Patent & Trademark Office (40 pages).
Office Action dated Apr. 17, 1995 in U.S. Appl. No. 08/200,636 (4 pages).
Supplemental Information Disclosure Statement dated Sep. 11, 1995 in U.S. Appl. No. 08/200,636 (7 pages).
U.S. Appl. No. 08/437,781, filed May 9, 1995 with U.S. Patent & Trademark Office (84 pages).
Office Action dated Nov. 1, 1996 in U.S. Appl. No. 08/437,781 (2 pages).
U.S. Appl. No. 09/639,612, filed Aug. 15, 2000 with U.S. Patent & Trademark Office (67 pages).
International Search Report, International Serial No. PCT/US2009/055397, dated Oct. 13, 2009.
International Search Report dated Sep. 28, 2009 of International Searching Authority for Application No. PCT/US2009/053724 (2 pages).

(56) References Cited

OTHER PUBLICATIONS

International Search Report dated Sep. 28, 2009 of International Searching Authority for Application No. PCT/US2009/053735 (2 pages).
International Search Report dated Sep. 23, 2009 of International Searching Authority for Application No. PCT/US2009/053762 (2 pages).
International Search Report dated Oct. 14, 2009 of International Searching Authority for Application No. PCT/US2009/053751 (2 pages).
International Search Report dated Apr. 13, 2010 of International Searching Authority for Application No. PCT/US2009/055380 (2 pages).
International Search Report dated Oct. 13, 2009 of International Searching Authority for Application No. PCT/US2009/055397 (2 pages).
Office Action dated Oct. 9, 2007 in U.S. Appl. No. 10/980,425 (16 pages).
Office Action dated Apr. 7, 2008 in U.S. Appl. No. 10/980,425 (20 pages).
Office Action dated Jul. 17, 2008 in U.S. Appl. No. 10/980,425 (3 pages).
Office Action dated Oct. 29, 2008 in U.S. Appl. No. 11/325,530 (11 pages).
Office Action dated Jun. 26, 2009 in U.S. Appl. No. 11/325,530 (13 pages).
Office Action dated Oct. 19, 2009 in U.S. Appl. No. 11/325,530 (6 pages).
Dr. Nicole Rotter, J. Aigner, A. Naumann, H. Planck, C. Hammer, G. Burmester, M. Sittinger; abstract of article entitled "Cartilage Reconstruction in Head and Neck Surgery: Comparison of Resorbable Polymer Scaffolds for Tissue Engineering of Human Septal Cartilage", in Journal of Biomedical Materials Research, vol. 42, Issue 3, pp. 347-356, Dec. 5, 1998; presumably published by John Wiley & Sons, Inc.; Abstract only is attached hereto; Abstract was downloaded from Internet at site for Wiley Online Library on Oct. 25, 2010 at http://onlinelibrary.wiley.com.
Robert J. Klebe; article entitled "Cytoscribing: A Method for Micropositioning Cells and the Construction of Two-and Three-Dimensional Synthetic Tissues", Experimental Cell Research 179 (1988) 362-373, published by Academic Press, Inc.
Emanuel Sachs, Michael Cima, James Bredt, Alain Curodeau, Tailin Fan, and David Brancazio; article entitled "Cad-Casting: Direct Fabrication of Ceramic Shells and Cores by Three Dimensional Printing", Manufacturing Review vol. 5, No. 2, pp. 117-126, Jun. 1992, published by American Society of Mechanical Engineers.
Joseph P. Vacanti, Martin A. Morse, W. Mark Saltzman, Abraham J. Domb, Antonio Perez-Atayde, and Robert Langer; article entitled "Selective Cell Transplantation Using Bioabsorbable Artificial Polymers as Matrices", Journal of Pediatric Surgery, vol. 23, No. 1, pp. 3-9, Jan. 1988, published by Grune & Stratton, Inc.
N.R. Boeree, J. Dove, J.J. Cooper, J. Knowles, and G.W. Hastings, article entitled "Development of a Degradable Composite for Orthopaedic Use: Mechanical Evaluation of an Hydroxyapatite-Polyhydroxybutyrate Composite Material", Biomaterials, vol. 14, No. 10, pp. 793-796, 1993, published by Butterworth-Heinemann Ltd.
R.B. Martin, M.W. Chapman, N.A. Sharkey, S.L. Zissimos, B. Bay, and E.C. Shors, article entitled "Bone Ingrowth and Mechanical Properties of Coralline Hydroxyapatite 1 Yr After Implantation", Biomaterials, vol. 14, No. 5, pp. 341-348, 1993, published by Butterworth-Heinemann Ltd.
Article entitled "Fractal" (nine pages), published on the Internet by the online encyclopedia Wikipedia; downloaded from the internet on Dec. 14, 2006 in the United States from the following address: http://en.wikipedia.org/wiki/Fractals.
Editor in Chief Sybil P. Parker, p. 799 (showing entries from "fp" to "fracture test") of McGraw-Hill Dictionary of Scientific and Technical Terms, Fifth Edition, published by McGraw-Hill, Inc., 1994, New York.

Office Action dated Oct. 31, 2008 in U.S. Appl. No. 10/980,425 (20 pages).
Office Action dated Oct. 20, 2006 in U.S. Appl. No. 11/060,377 (10 pages).
Written Opinion dated Sep. 28, 2009 of International Searching Authority for Application No. PCT/US2009/053724 (8 pages).
Written Opinion dated Sep. 28, 2009 of International Searching Authority for Application No. PCT/US2009/053735 (7 pages).
Written Opinion dated Sep. 23, 2009 of International Searching Authority for Application No. PCT/US2009/053762 (4 pages).
Written Opinion dated Oct. 14, 2009 of International Searching Authority for Application No. PCT/US2009/053751 (6 pages).
Article entitled "Rolled Threads." (3 pages), published on the Internet by the online encyclopedia Wikipedia; downloaded from the internet on Aug. 24, 2009 in the United States from the following address: http://en.wikipedia.org/wiki/File:American_Machinists_Handbook--2e--p23--v001.png.
Written Opinion dated Apr. 13, 2010 of International Searching Authority for Application No. PCT/US2009/055380 (8 pages).
Written Opinion dated Oct. 13, 2009 of International Searching Authority for Application No. PCT/US2009/055397 (9 pages).
Unknown Author, article entitled "MacroPore Resorbable Technology: An Overview", Scientific Data Series in Resorbable Fixation, MKT004 Rev. 6/01, pp. 1-8; distributed by Medtronic Sofamor Danek, 1800 Pyramid Place, Memphis TN 38132, (Jun. 2001).
Ralph E. Holmes, M.D., Stefan M. Lemperle, M.D., and Christopher J. Calhoun, M.B.A., article entitled "Protected Bone Regeneration", Scientific Data Series in Resorbable Fixation, MKT003 Rev. 6/01, pp. 1-10; distributed by Medtronic Sofamor Danek, 1800 Pyramid Place, Memphis TN 38132, (Jun. 2001).
D.R. Sumner, T.M. Turner, R.M. Urban, R.M. Leven, M. Hawkins, E.H. Nichols, J.M. McPherson, J.O. Galante, article entitled "Locally Delivered rhTGF-B2 Enhances Bone Ingrowth and Bone Regeneration at Local and Remote Sites of Skeletal Injury", Journal of Orthopaedic Research 19 (2001) pp. 85-94, published by Elsevier Science Ltd.
International Search Report dated May 18, 2005 of International Searching Authority for Application No. PCT/US2004/036997 (3 pages).
U.S. Appl. No. 08/048,408, filed Apr. 15, 1993 with U.S. Patent & Trademark Office (108 pages).
Preliminary Amendment dated Jul. 8, 1993 and filed in U.S. Appl. No. 08/048,408 with U.S. Patent & Trademark Office (12 pages).
Machine English translation of JP 2587625 (10 pages), Oct. 28, 2010.
International Preliminary Report on Patentability dated May 8, 2006 of International Searching Authority for Application No. PCT/US2004/036997 (6 pages).
Written Opinion dated May 18, 2005 of International Searching Authority for Application No. PCT/US2004/036997 (5 pages).
Communication and supplementary European search report dated Nov. 14, 2008 from European Patent Office in application No. 04818642 (3 pages).
Office Action dated Jun. 25, 2010 from European Patent Office in application No. 04818642 (5 pages).
International Search Report dated Mar. 12, 2007 of International Searching Authority for PCT/US2005/019045 (3 pages).
International Preliminary Report on Patentability dated Aug. 21, 2007 of International Searching Authority for Application No. PCT/US2005/019045 (7 pages).
Written Opinion dated Mar. 12, 2007 of International Searching Authority for Application No. PCT/US2005/019045 (6 pages).
Office Action dated May 7, 2007 in U.S. Appl. No. 11/060,377 (13 pages).
Office Action dated Aug. 20, 2007 in U.S. Appl. No. 11/060,377 (3 pages).
Office Action dated Feb. 20, 2008 in U.S. Appl. No. 11/060,377 (5 pages).
Office Action dated Sep. 2, 2008 in U.S. Appl. No. 11/060,377 (7 pages).
Office Action dated Dec. 15, 2008 in U.S. Appl. No. 11/060,377 (8 pages).
Interview Summary dated Mar. 5, 2009 in U.S. Appl. No. 11/060,377 (2 pages).

(56) References Cited

OTHER PUBLICATIONS

Office Action dated May 27, 2009 in U.S. Appl. No. 11/060,377 (7 pages).
Communication dated Apr. 11, 2013 from Canadian Intellectual Property Office for Canadian patent application No. 2,735,236 (3 pages).
Communication dated May 22, 2013 from European Patent Office for European Patent Application No. 09807307.5-1506 (1 page).
Communication dated May 2, 2013 from European Patent Office for European Patent Application No. 09807307.5-1506, including Supplementary European Search Report and opinion (7 pages).
Translation of Japanese Office Action issued for Japanese Patent Application No. 2011-525242 (2 pages).
Communication from Canadian Intellectual Property Office dated Jan. 11, 2013 for Canadian patent application No. 2,735,235 (2 pages).
International Preliminary Report on Patentability dated Feb. 15, 2011 for PCT/US2009/053724 (9 pages).
International Preliminary Report on Patentability dated Feb. 15, 2011 for PCT/US2009/053735 (8 pages).
International Preliminary Report on Patentability dated Feb. 15, 2011 for PCT/US2009/053751 (7 pages).
International Preliminary Report on Patentability dated Feb. 15, 2011 for PCT/US2009/053762 (5 pages).
International Preliminary Report on Patentability dated Mar. 1, 2011 for PCT/US2009/055380 (9 pages).
International Preliminary Report on Patentability dated Mar. 1, 2011 for PCT/US2009/055397 (10 pages).
Machine English translation of JP 2587625 (10 pages); downloaded from the Internet on Oct. 28, 2010 and Nov. 11, 2010 (as indicated on the bottom of the pages of the document).
Photos 309 and 310 show a poster of which Applicant is aware. By disclosing these photos, Applicant is making no statement as to whether or not these photos are material or are prior art relative to the present application.

* cited by examiner

ORTHOPAEDIC IMPLANT

CROSS REFERENCE TO RELATED APPLICATIONS

This is a non-provisional application based upon U.S. provisional patent application Ser. No. 61/092,890, entitled "ORTHOPAEDIC IMPLANT", filed Aug. 29, 2008, which is incorporated herein by reference. Further, this is a continuation-in-part of U.S. patent application Ser. No. 12/540,760, now U.S. Pat. No. 8,475,505, entitled "ORTHOPAEDIC SCREWS", filed Aug. 13, 2009, which is incorporated herein by reference. U.S. patent application Ser. No. 12/540,760 is a non-provisional application based upon U.S. provisional patent application Ser. No. 61/088,383, entitled "ORTHOPAEDIC SCREWS", filed Aug. 13, 2008, which is incorporated herein by reference.

BACKGROUND OF THE INVENTION

1. Field of the Invention

The present invention relates to implants, and, more particularly, to orthopaedic implants.

2. Description of the Related Art

A number of solid metal and resorbable polymer (e.g. PLLA, PGA) screws are known. These screws are generally meant to provide short term (9 months or less) attachment of the soft tissue to the bone until healing and integration can occur.

There are a number of problems associated with the known metal and resorbable screws. Due to the density of the metals that are used in the solid metal screws, it is difficult to examine bone or soft tissue that is near the screw via x-ray, CT, or MRI scan. The screw causes a significant 'white-out' in the region of the screw. Tissue healing and integration around the screw is critical to the success of the surgery, thus the ability to evaluate the tissue near the screw is valuable. In addition, the solid metal screws have issues with poor initial fixation and later pull-out of the soft tissue (e.g. pull out of an ACL from the bone) does occur. These are painful and can require follow-up surgery. Certainly any improvements to reduce the rate of pull-out and additional surgery would be desirable.

With respect to the known resorbable screws, issues with poor initial fixation and pull-out also exist. The rate of resorbtion of the polymer can be difficult to control and can occur too quickly for a given patient, increasing the risk of soft tissue pull-out. Further, resorbable materials have been shown to induce fibrous tissue formation between the resorbable implant and the bone, increasing the risk of soft tissue pull-out. This may be due to the local chemistry created as the polymer dissolves.

Further, one individual may need to undergo multiple surgeries on a given joint. However, the more material and/or hard material that remains relative to an orthopaedic implant, the greater the difficulty that material can cause in future surgeries.

What is needed in the art is an orthopaedic screw that allows for more effective fixation of the tissue and visualization with known imaging devices of the tissue near and surrounding the screw. Further, what is needed in the art is an orthopaedic internal fixation device which includes at least two different structural materials, one such structural material being non-resorbable relative to a corporeal body.

SUMMARY OF THE INVENTION

The present invention provides porous screws and screws that can deliver therapeutic agents. Further, the present invention provides a porous screw for attaching various soft tissues to bone, and/or for attaching bone to bone, and/or for delivering therapeutic agents (for example biologics or drugs) to soft tissue and/or bone. Potential uses include, but are not limited to, ACL and PCL reconstruction, medial collateral ligament repair, lateral collateral ligament repair, posterior oblique ligament repair, iliotibial band tenodesis reconstruction, patellar ligament and tendon repair, pedicle screws for spine repair, bone fracture fixation screw, and drug eluting implant (non-load bearing) for delivery of therapeutics.

Further, the present invention provides an orthopaedic internal fixation device which includes at least two different structural materials, one such structural material being non-resorbable relative to a corporeal body.

An embodiment of the present invention provides an orthopaedic screw having a plurality of regions, at least one of which may be porous. The orthopaedic screw includes a head, a tip and at least one thread. The porosity of the screw of the present invention can vary within the part or region, including changes in pore shape, size and density. These characteristics can vary along the length of the screw axis and/or radially (from the outer diameter to the axis).

The orthopaedic screw of the present invention may further include at least one solid region formed of any implantable polymer, reinforced polymer or metal. The solid region of material may be, for example, at the outer portion of the threads and the leading tip of the screw due to the high stresses present during insertion. The solid region may further include the head of the orthopaedic screw of the present invention.

The materials to create the orthopaedic screw of the present invention can be any implantable polymer, metal or ceramic, or any combination thereof. Possible polymers include polyetheretherketone (PEEK), polyetherketone (PEK), polyaryletherketone (PAEK), polyethylene, and resorbable polymers such as polylactic acid (PLA) and polyglycolic acid (PGA).

The thread of the orthopaedic screw of the present invention may be continuous or discontinuous and be a single or multiple lead thread. The inventive screw may further be cannulated or non-cannulated.

The orthopaedic screw of the present invention may further be used to locally deliver therapeutic agents that promote positive tissue response (e.g. increased growth rate, decreased inflammatory response). Such therapeutic agents include, but are not limited to, hydroxyapatite, drugs and biologics.

Another embodiment of the orthopaedic screw of the present invention provides for immediate delivery of a therapeutic agent through channels and/or holes and reservoirs for long-term delivery of a therapeutic agent. Access to the delivery channels, holes and/or reservoirs may be gained by provision of a self-sealing polymer diaphragm which can allow for direct interface with a needle at the time of surgery of post-surgery. Alternatively, a removable cap made of PEEK or other implantable material may provide access to and seal the medicine delivery features of the inventive screw.

Another embodiment of the inventive orthopaedic screw composed of radiolucent material includes a radiopaque marker to indicate position and orientation of the implant on an x-ray, fluoroscope, or similar diagnostic tool. The markers can be made of any number of more dense implantable materials. Options include, but are not limited to implantable metals (stainless steel, titanium, or titanium alloys for example), barium sulfate filled PEEK, carbon filled PEEK, and other polymers with radiopaque material (such as barium sulfate or zirconium dioxide). Examples of the marker structure include one or more of the following: a pin filling some or all of the cannula of a cannulated screw, one of material layers of the inventive screw if manufactured by layering, all or some of the threads, a cross pin, or the head or tip of the screw. The opacity and/or amount of radiopaque material can be controlled so that the marker does not prevent evaluation of the tissue near the screw by x-ray or other diagnostic methods.

The invention in another form is directed to an orthopaedic implant system, including an orthopaedic implant implantable at a selected location within a corporeal body. The implant includes a first structural material and a second structural material. The first structural material is non-resorbable relative to the corporeal body and is different relative to the second structural material. The implant is an internal fixation device.

The invention in another form is directed to a method of using an orthopaedic implant system, the method including the steps of: providing an orthopaedic implant including a first structural material and a second structural material, the first structural material being non-resorbable relative to a corporeal body and being different relative to the second structural material, the implant being an internal fixation device; and implanting the orthopaedic implant at a selected location within the corporeal body.

An advantage of the present invention is that the porous nature of the inventive orthopaedic screw and the ability to deliver therapeutic agents to the surrounding tissue promotes successful tissue integration. Such local delivery of therapeutic agents can aid in such issues as improving the attachment strength of soft tissue to bone in reconstructive surgeries, improving the attachment strength of bone to screw, and strengthen bone in osteoarthritic or osteoporotic patients.

Another advantage is that the orthopedic screw of the present invention can effectively be utilized for long term or short term delivery of therapeutic agents. Another advantage is that the therapeutic agent can be pre-loaded into the device at the factory or loaded by the surgeon before, during or after surgery.

Yet another advantage is that it provides orthopaedic screws and other implants with multiple materials and/or therapeutic delivery capability.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

The present invention provides a device which can have a porous nature and can have the ability to deliver therapeutic agents. The porous nature of the device of the present invention and the ability of the device of the present invention to deliver therapeutic agents therethrough addresses existing deficiencies in the known art by promoting successful tissue integration.

The present invention provides a screw that is porous and/or can deliver therapeutic agents to the surrounding tissue. The materials to create this screw can be any implantable polymer, metal or ceramic or combinations of these. Possible polymers include PEEK (Poly(etheretherketone)), PEK (Poly(etherketone)), PAEK (poly(aryletherketone)), polyethylene, and resorbable polymers such as PLA (Poly(lactic acid)) and PGA (poly(glycolic acid)). Likely first candidates are PEEK, reinforced PEEK (reinforcing materials include but are not limited to carbon fiber/particles/nanotubes, barium sulfate, zirconia) and titanium/titanium alloys. The screw of the present invention can include, but does not need to include, the ability to deliver therapeutic agents (such as drugs or biologics) to the surrounding tissue. The therapeutic agent can be selected by the surgeon before the surgery, at the time of surgery, or at any point in time thereafter. In addition, the therapeutic agent can be pre-loaded into the device at the factory through currently acceptable practices or loaded by the surgeon before, during, or after surgery (as a follow-up procedure).

The screw of the present invention can be porous but does not need to be porous.

Figure 1:
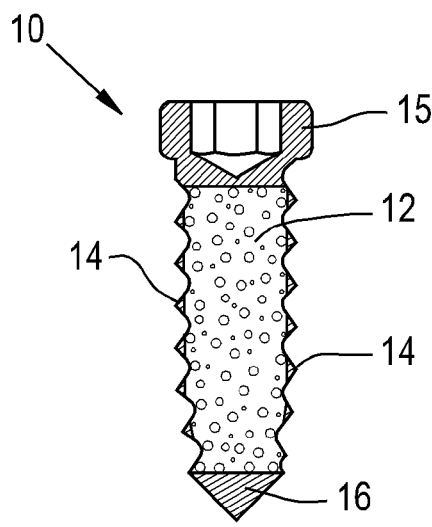
FIG. 1 is a section view of a porous screw with solid outer threads and tip according to the present invention.

Screw 10 of the present invention can be fully porous or have select regions of solid material. For example, screw 10 may include porous region 12 and a solid region of material at the outer portion of threads 14 and leading tip 16 of screw 10. The solid region of material at the outer portion of threads 14 and leading tip 16 of screw 10 may be desired due to the high stresses these regions can see during screw insertion (see FIG. 1). In addition, a very rough porous structure on the outer portion of the threads can cause insertion of the screw to be difficult due to its potential to grab versus slide past or cut through bone/soft tissue. The head 15 of screw 10 may be solid. This solid material can be formed of any implantable polymer, reinforced polymer, or metal.

Figure 2A:
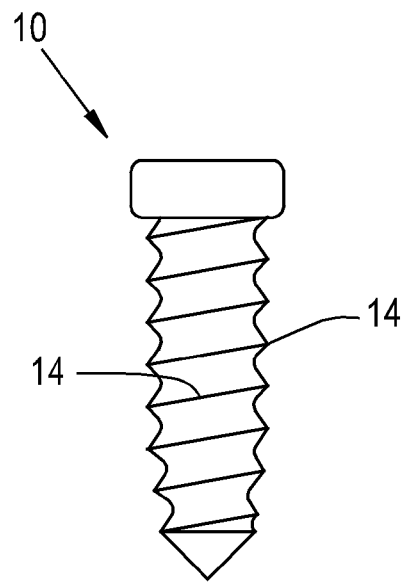
FIG. 2A is a side view of a screw having a continuous thread.
Figure 2B:
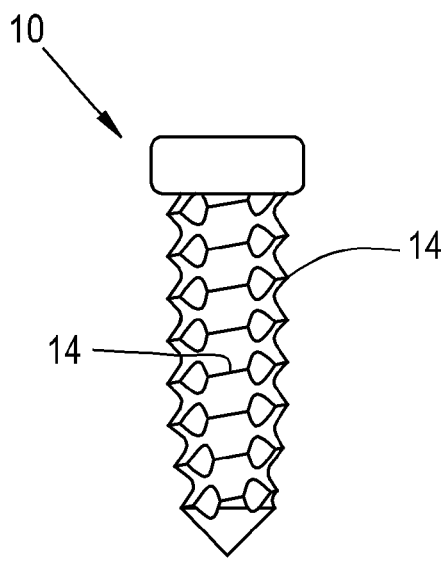
FIG. 2B is a side view of a screw having a discontinuous thread.

Thread 14 can be continuous (see FIG. 2A) or discontinuous (see FIG. 2B) and be a single or multiple lead thread.

The porosity of the screw can vary within the region(s), including changes in pore shape, size, and density. These characteristics can vary along the length of the screw axis and/or radially (from the outer diameter to the axis).

Another way of improving integration of the surrounding tissue is to deliver therapeutic agents that promote positive tissue response (e.g. increased growth rate, decreased inflammatory response). The orthopaedic screw of the present invention can be used to locally deliver such therapeutic agents to the tissue surrounding the device. Such local delivery of therapeutic agents can aid in such issues as improving the attachment strength of soft tissue to bone in reconstructive surgeries, improving the attachment strength of bone to the screw, and strengthen bone in osteoarthritic or osteoporotic patients. Therapeutic agents include, but are not limited to, hydroxyapatite, drugs, and biologics.

Screws allowing for localized delivery of therapeutic agents, according to the present invention, can be, but need not be, porous. Porous screws according to the present invention can, but need not, allow for localized delivery of therapeutic agents.

Figure 3:
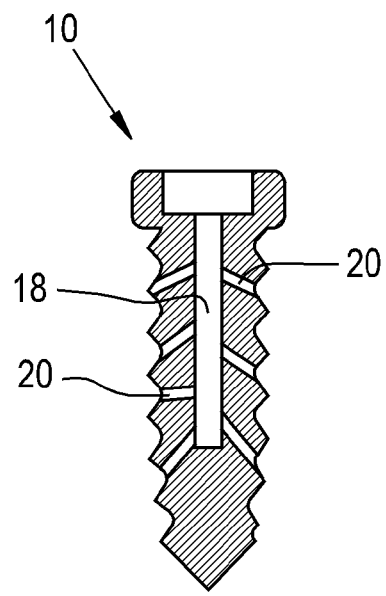
FIG. 3 illustrates an implant according to the present invention for immediate delivery of a therapeutic agent.
Figure 4:
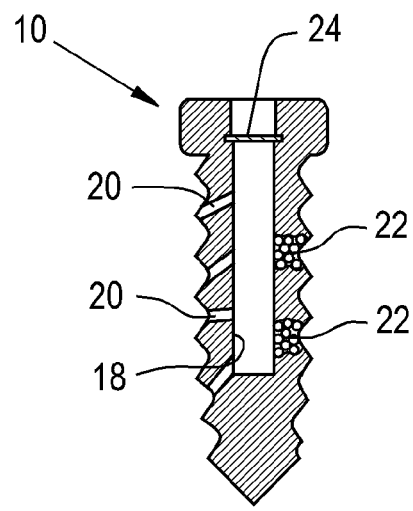
FIG. 4 illustrates an implant according to the present invention for immediate or sustained delivery of a therapeutic agent.
Figure 5:
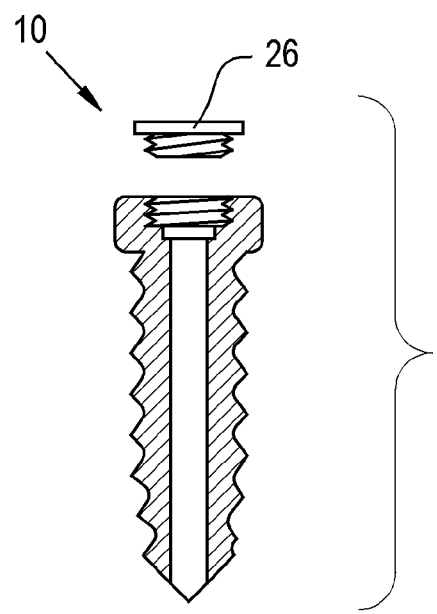
FIG. 5 illustrates a therapeutic agent delivery implant according to the present invention with sealing cap.
Figure 6A:
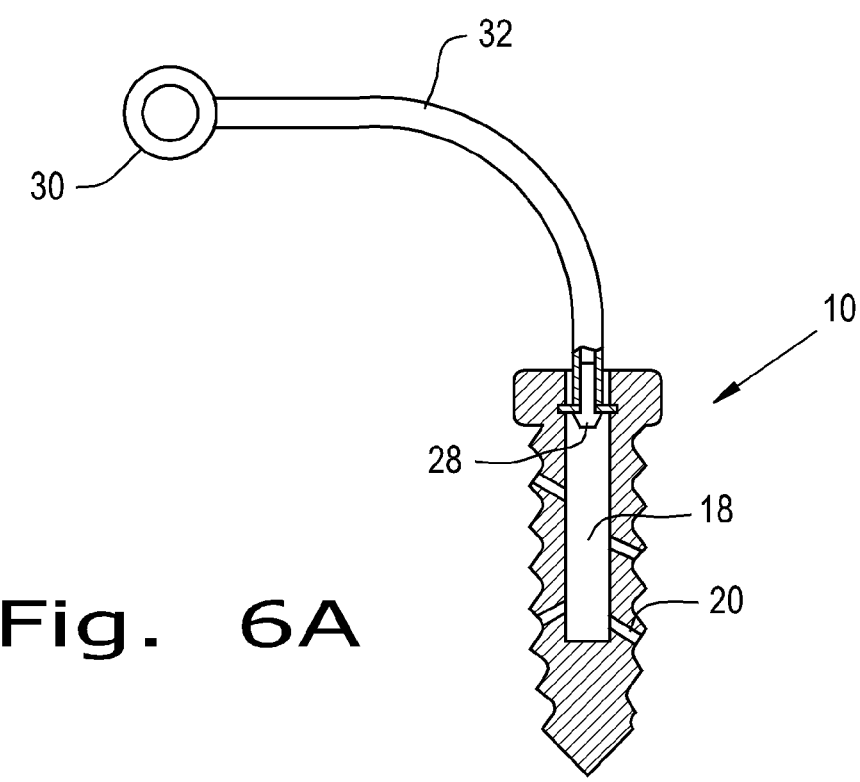
FIG. 6A illustrates an implant according to the present invention with port attachment features.
Figure 6B:
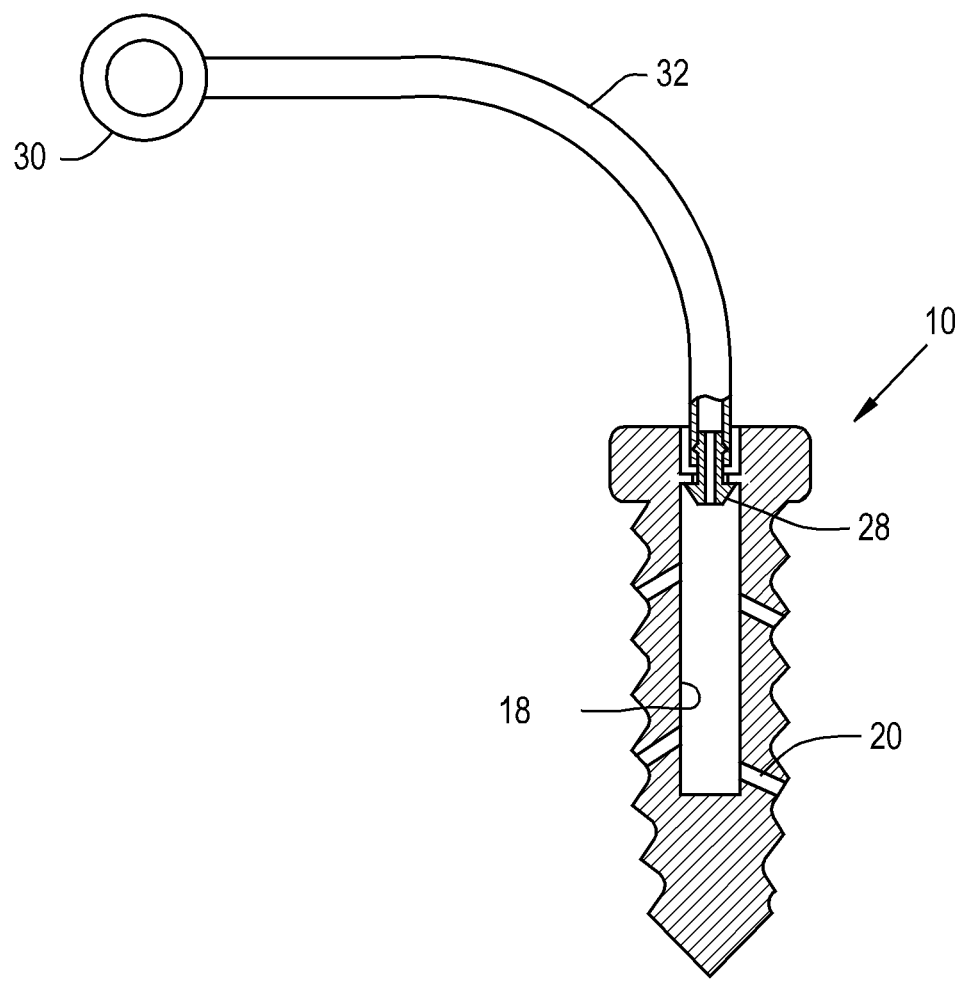
FIG. 6B illustrates an implant according to the present invention with port attachment features.

Screw 10 can contain reservoirs 18 for the long-term delivery of the therapeutic agents, as illustrated in FIG. 4 and/or channels/holes 20, as illustrated in FIG. 3, for immediate, local delivery of therapeutic agents. Screw 10 can further include a plurality of interconnected pores 22 allowing for local delivery of a therapeutic agent to the surrounding tissue, as shown in FIG. 4. These options are described as follows:
1. Long term delivery.
    a. Reservoirs. One or more reservoirs 18 can allow for the long term (hours to weeks) delivery of the therapeutic agents. Access to delivery channels 20, reservoir 18, etc. of screw 10 is gained by several ways including:
        i. Self-sealing polymer diaphragm 24 can allow for direct interface with a needle at the time of surgery or post-surgery (see FIG. 4).
        ii. A removable cap 26 made of PEEK or another implantable material can also provide access to the therapeutic agent delivery features and seal these features after delivery of the therapeutic agent (FIG. 5). A tool that facilitates insertion of the screw could also aide in assembling cap 26 to the screw.
    b. Connect to another device. Access to the therapeutic agent delivery features of the screw can be provided by interfacing screw 10 with a device designed to deliver therapeutic agents from subcutaneous to elsewhere in the body (e.g. a port that is frequently used to deliver therapeutic agents from sub-skin to a vein deeper in the chest cavity). The last option can include attachment feature 28 on screw 10 that directly interfaces with port 30, interfaces with catheter 32 (which interfaces with the port 30) or interfaces with an additional component, which can be attached to screw 10 to interface with port 30 or catheter 32—See FIGS. 6A and 6B). FIG. 6B shows an alternative attachment feature 28. Port 30 can have a septum (the center circle of port 30) for receiving an injection of a therapeutic agent.
2. Immediate delivery. No reservoir is required for this approach. The access means of the reservoir design above (self-healing polymer diaphragm 24 and removable cap 26) can also be used to access delivery channels 20 in this design. This design can also include a simple interface with a delivery tool. An example of this is a simple slip fit between a delivery needle and the screw's cannula.

A given screw can contain any or all of these options.

Cannulation

The screws can be cannulated or non-cannulated.

Radiopaque Markers—Polymer Implants

Figure 7A:
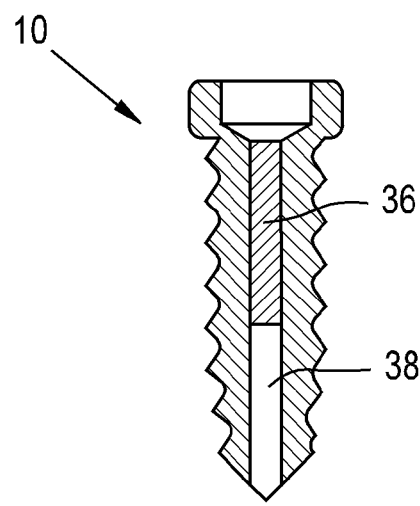
FIG. 7A illustrates an implant according to the present invention including a radiopaque marker.
Figure 7B:
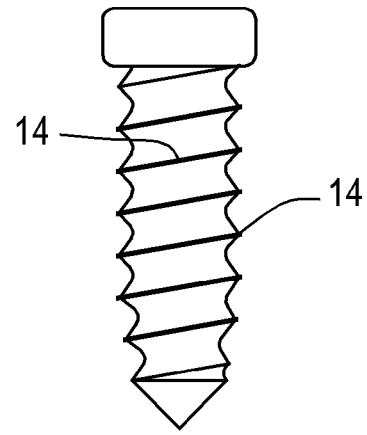
FIG. 7B illustrates an implant according to the present invention including a radiopaque marker.
Figure 7C:
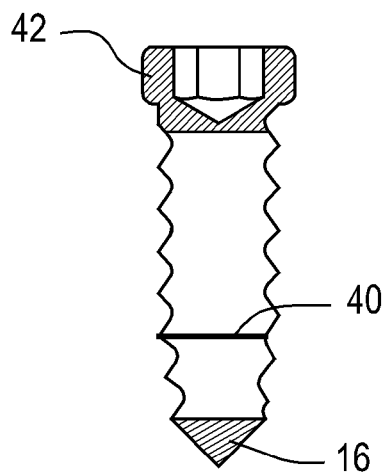
FIG. 7C illustrates an implant according to the present invention including a radiopaque marker.

If the implant according to the present invention is made of a radiolucent material (for example polymers such as PEEK), radiopaque markers can be included to indicate position and orientation of the implant on an x-ray, fluoroscope, or similar diagnostic tool. Markers can be made of any number of more dense implantable materials. Options include, but are not limited to, implantable metals (stainless steel, titanium, or titanium alloys for example), barium sulfate filled PEEK, carbon filled PEEK, or other polymers with radiopaque material (such as barium sulfate or zirconium dioxide). Examples of the marker design include one or more of the following: pin 36 filling some or all of cannula 38 of a cannulated screw, one of the material layers if the manufacturing method involves material layering (discussed below), all or some of threads 14, cross pin 40, or head 42 or tip 16 of the screw (see FIGS. 7A-C). The opacity and/or amount of radiopaque material can be controlled so that the marker does not prevent evaluation of the tissue near the screw by x-ray or other diagnostic ways (as occurs with current solid metal screws).

Sections (A) through (E) are discussed immediately below. These sections are as follows: (A) manufacturing options for making the porous screw according to the present invention; (B) how to bond parts containing polymer(s); (C) how to bond metal/metal alloy parts; (D) manufacturing options for making screw threads of a screw according to the present invention; and (E) and manufacturing options for cannulation according to the present invention. Sections (A) through (E) are discussed in reference to forming a screw according to the present invention. It is understood, however, that the discussion can be applied or adapted as necessary to other internal fixation devices.

A. Porous Structure—Manufacturing Options According to the Present Invention

Figure 8:
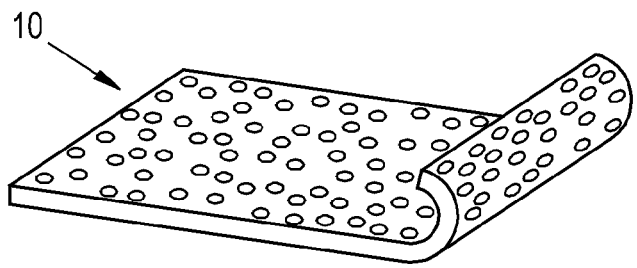
FIG. 8 is a schematic representation of a perspective view of a porous sheet to be rolled into a screw according to the present invention.
Figure 9:
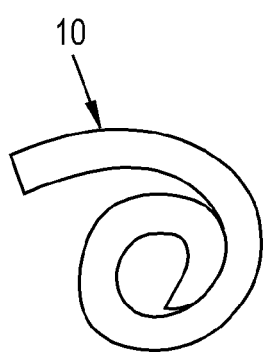
FIG. 9 is a schematic representation of an end view of the sheet of FIG. 8 during the rolling process.
Figure 10:
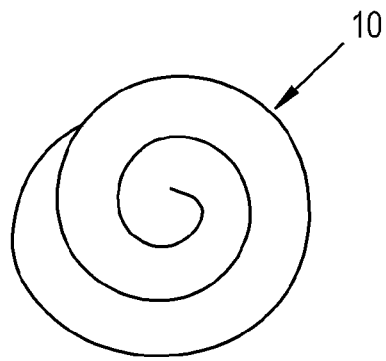
FIG. 10 is a schematic representation of a sectioned end view of the sheet of FIG. 8 after the rolling process.
Figure 11:
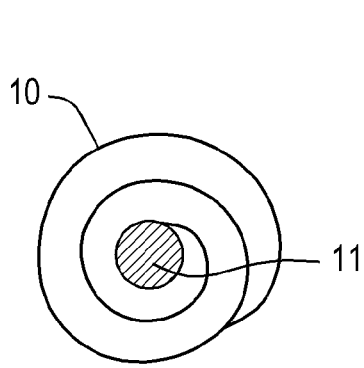
FIG. 11 is a schematic representation of the sheet of FIG. 8 after the rolling process.
Figure 12:
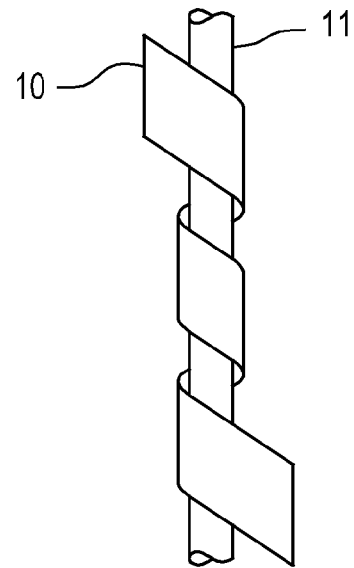
FIG. 12 is a schematic representation of a perspective view of a spiraled band of material.
Figure 13:
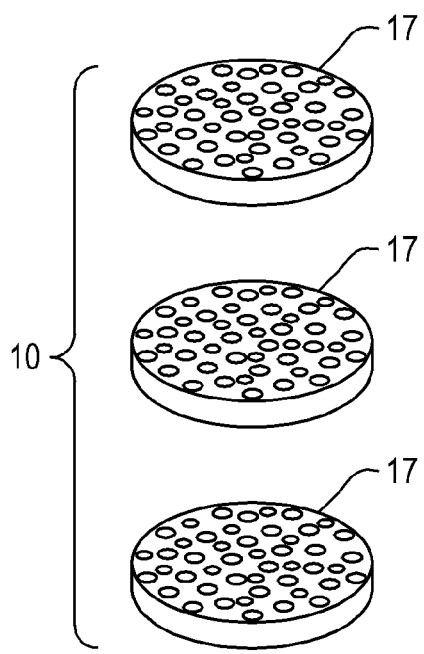
FIG. 13 is a schematic representation of a perspective view of screw layers exploded from one another according to the present invention.
Figure 14:
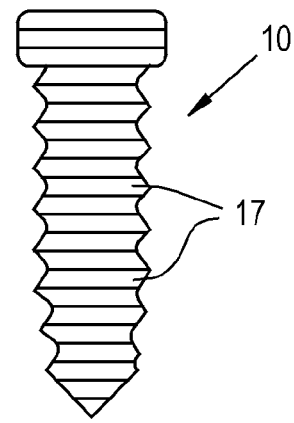
FIG. 14 is a schematic representation of a side view of a screw according to the present invention.
Figure 15:
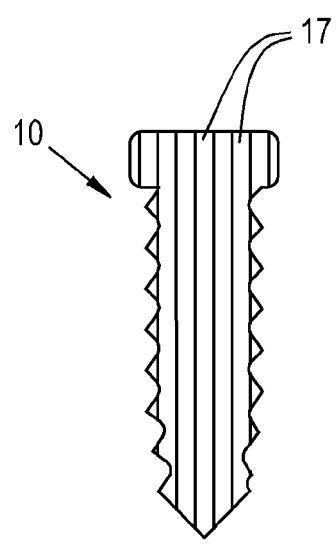
FIG. 15 is a schematic representation of a side view of a screw according to the present invention.

The porous structure of the present invention can be manufactured using a variety of methods. These manufacturing options according to the present invention include seven options as follows:

1. Rolled. A porous sheet can be, for example, rolled into a screw. This is essentially the reverse of making a radial, spiral cut that is parallel to the axis of the screw. Layers of different materials can be combined in this process. This process involves the following:
    a. Make a porous sheet with holes in a pattern so that they line up when rolled.
    b. Roll sheet (see FIGS. 8-11. FIG. 8 shows a porous sheet 10 according to the present invention to be rolled into a screw 10. FIG. 9 shows an end view of sheet 10 during the rolling process. FIG. 10 shows a sectioned end view of the final product, formed as a screw 10. FIG. 11 shows the sheet 10 with a center 11 formed as a cannula 11 (an open hole through the screw axis), or a porous rod 11, or a solid rod 11). This step can be performed with or without the aid of a center mandrel or rod.
        1. The sheet can be rolled without the aid of any center mandrels. This can create a cannulated screw. A biocompatible pin/rod can be inserted in any center hole and bonded to the screw to create a non-cannulated screw.
        2. The sheet can be rolled around a removable mandrel. This can create a cannulated screw. A biocompatible pin/rod can be inserted in any center hole and bonded to the screw to create a non-cannulated screw.
        3. Alternately the sheet can be rolled around and bonded to a biocompatible rod, creating a non-cannulated screw.
    c. Bond the rolled material.
2. Spiraled layers. This method is similar to the rolled approach, but this method involves bands of material that are wrapped around one another. The main difference between this method and that of rolling is that in this method, the bands of material translate along the axis while they are wrapped (see FIG. 12. FIG. 12 shows an example of a spiraled band of material 10, the material not having pores). Bands of several materials can be combined and intertwined. All bands can have the same direction and pitch of winding or different directions and pitches. These bands can be wrapped around a mandrel 11 that is later removed to aid in bonding and to create a cannula. They can also be wrapped around a pin 11 which they are then bonded to, creating a non-cannulated screw. An alternate option for creating a non-cannulated screw is to create the screw with or without the aid of a mandrel, then insert and bond a pin within the center hole of the screw.
3. Layered/stacked. Make a number of layers that are stacked and bonded to create the screw. These layers can be parallel to one another. The faces of the layers are perpendicular to the axis of the screw, parallel to it, or any other angle of orientation. To reduce secondary operations, alignment of one layer to another may be desirable. Alignment of layer to layer can be achieved by such ways as alignment fixtures that line up the center cannula (if the screw is cannulated) of each layer to one another (by way of a pin for example), fixtures or implant components/features that align pore or thread features to one another, or fixtures or implant components/features that align features on the outer diameter of each layer to one another. Features can also be created within a given layer to aid in alignment and/or assembly (such as grooves and mating protrusions). FIGS. 13-15 show the stacked manufacturing method. FIG. 13 shows layers 17 of the screw 10 exploded from one another and stacking in the direction of the arrows. FIG. 14 shows a side view of screw 10 with stacked layers 17 perpendicular to the longitudinal axis of screw 10. FIG. 15 shows a side view of screw 10 with stacked layers 17 parallel to the longitudinal axis of screw 10.

Note: The holes in FIGS. 13-15 can be created by, for example, laser cutting, punching, etching, electrical discharge machining, plasma etching, electroforming, electron beam machining, water jet cutting, stamping, or machining. For polymer based materials, they can be created as the sheets are created by, for example, extruding, injection molding, or hot stamping.

4. Dissolvable material.
    a. One method involves creating a mixture of powdered implantable material (e.g. PEEK) and a powder (e.g. salt) that is soluble in something in which the implantable material is not soluble (such as water, isopropyl alcohol for the PEEK example). The mixture is then heated to bond the implantable particles together. Pressure can also be applied to aid in the bonding of particle to particle. Heat can be created by convection or other ways (such as coating the powder with a material that absorbs a given range of energy waves—such as laser waves—and causes heating. (e.g. Clearweld coating by Gentex® Corporation)). Finally, dissolve away the filler to create the porous implantable material. This method can create net shape parts or raw material shapes from which individual parts can be created.
    b. Another method involves mixing an implantable polymer with a dissolvable material such as described above. The mixture is then pelletized and then injection molded to an intermediary or the final part shape. The filler is dissolved away to create the porous implantable polymer.
5. Stereolithography.
6. Laser or electron beam sintering of powdered material.
7. A combination of the above methods: for example, using the dissolvable method to create microporous sheets of PEEK, then stamping larger pores and stacking to create a screw.

B. How to Bond Parts Containing Polymer(S)

Options for Bonding Processes

1. Heat. Heat can be generated in several ways:
    a. Ultrasonic welding—use ultrasonic waves to create heat at the interface of layers.
    b. Heat staking—use a heated tool to cause melting between the layers.
    c. Vibratory welding.
    d. Laser welding.
    e. Convection—use an oven to create heat to cause bonding.
    f. Intermediary layer—for example, use a material that can absorb energy waves that pass through the polymer (for example PEEK) without causing damage. The absorbed energy will cause localized heating. An example of such a coating is Clearweld by Gentex® Corporation. The laser waves that Clearweld absorbs pass through the PEEK without causing damage, allowing the layers to be melted together without large scale damage to the PEEK.

2. Chemical.
   a. Adhesives—a secondary material (such as adhesive) can be used to bond the material.
   b. Solvent bonding—a material in which the polymer or reinforced polymer is soluble can be applied to the sheet surfaces allowing multiple surfaces to be bonded to one another.
   c. Overmolding—overmolding of the polymer or reinforced polymer can provide a chemical bonding
3. Mechanical.
   a. Overmolding—overmolding of a polymer or reinforced polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.
   b. Features are provided within the layers or by a separate component which provides a mechanical lock—e.g. a pin, snap lock connection, dove-tail, tongue-groove, rivet, melting tabs to create a mechanical lock, etc.
   c. Some adhesives provide a mechanical bond in addition to or instead of a chemical bond.
4. Combinations of any/all of the above methods.

Order of Processes
1. Bond all layers together at once—especially attractive for methods utilizing energy waves to trigger bonding (e.g. Clearweld coating by Gentex® Corporation or ultraviolet light curable adhesives).
2. Simultaneously bond and roll/stack layers at once—again, may be especially attractive for methods utilizing energy waves to trigger bonding (e.g. if light cannot penetrate all layers of a rolled design in order to activate an adhesive, the rolling operation could take place in a light box allowing for a continuous rolling and adhesive curing operation.
3. Roll/stack layers and bond in increments. This could add a single layer at a time or multiple layers.

C. How to Bond Metal/Metal Alloy Parts
Options for Bonding Processes
1. Heat.
   a. Laser welding—layers can be laser welded in a number of locations. Two or more layers or wraps of material can be welded together at once depending on the size of the part and alignment of the pores (the laser can access several layers to be bonded through the porosity).
   b. Spot welding—traditional spot welding can be used to bond two or more layers/wraps of material.
   c. Diffusion bonding/sintering.
   d. Vibratory welding.
   e. Ultrasonic welding.
2. Adhesives.
3. Mechanical ways. Features are provided within the layers or by a separate component which provides a mechanical lock—e.g. a pin, snap lock connection, dove-tail, tongue-groove, rivet, melting tabs to create a mechanical lock etc.
4. Overmolding with an implantable polymer. Overmolding of PEEK or another implantable polymer can create a mechanical lock between components on a micro or macro scale (microscale—the molded material locks with surface asperities of the existing material. Macroscale—features such as tongue-groove connections or undercuts). The overmolded material can be a separate component from the layers or one layer can be overmolded onto another layer.

Order of Processes
As with the polymer materials discussed above, two or more layers of metal can be bonded during increments or as a continuous stacking/bonding process.

Figure 16:
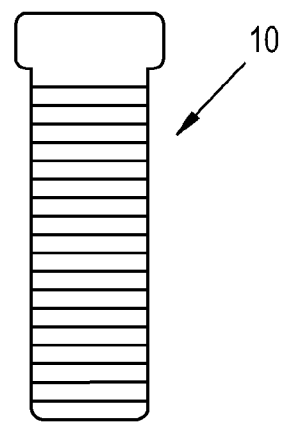
FIG. 16 is a schematic representation of a screw blank according to the present invention.
Figure 17:
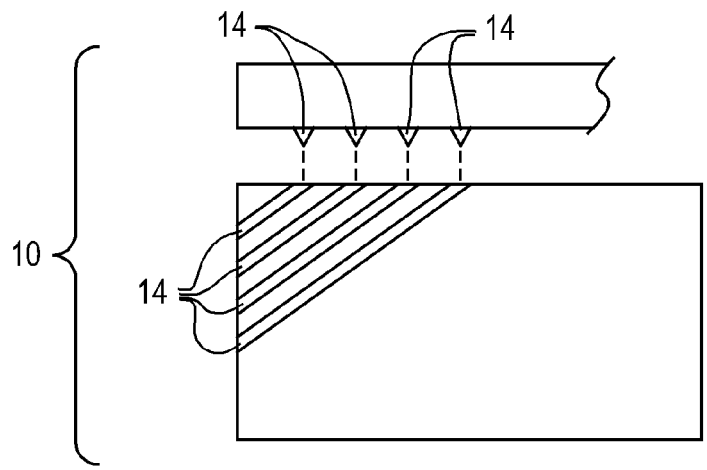
FIG. 17 is a schematic representation of a sheet showing raised threads formed prior to rolling.
Figure 18:
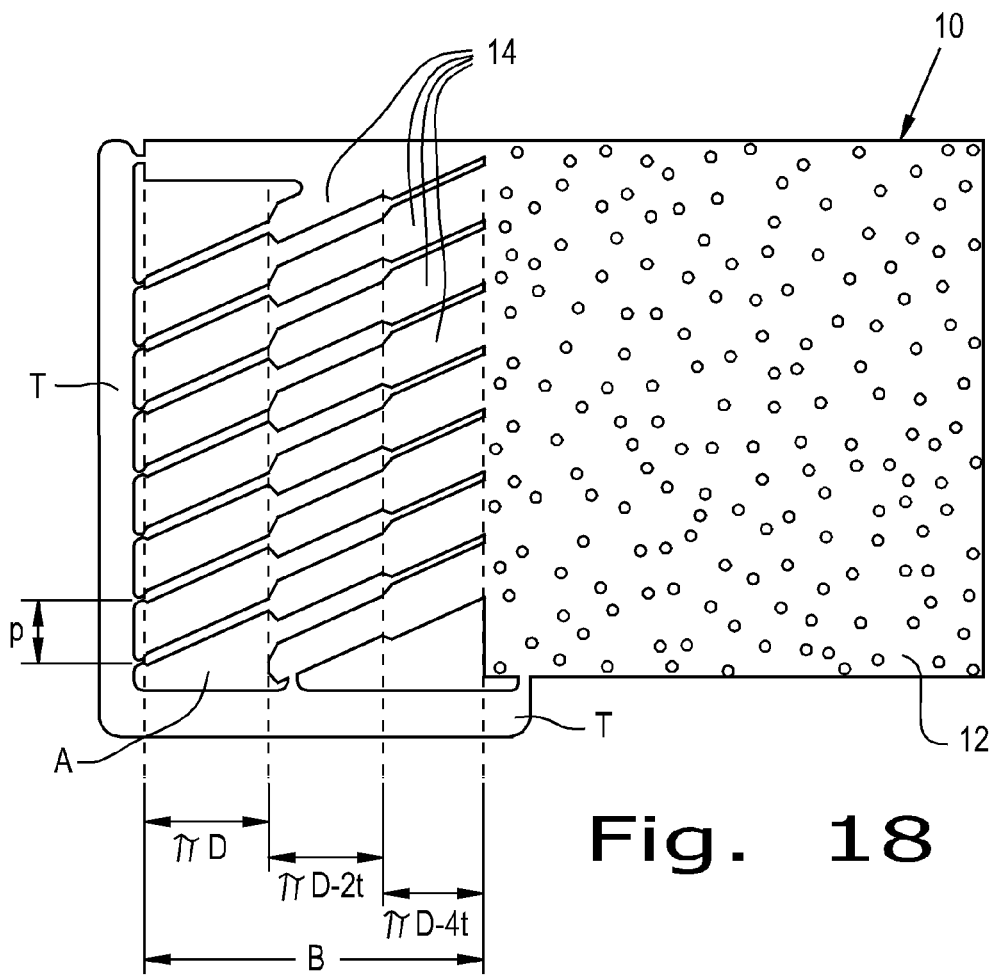
FIG. 18 is a schematic representation of a sheet showing threads formed by material removal prior to rolling.
Figure 19:
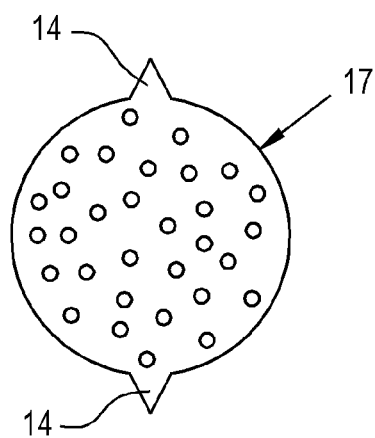
FIG. 19 is a schematic representation of a plan view of a sheet showing threads formed prior to stacking.
Figure 20:
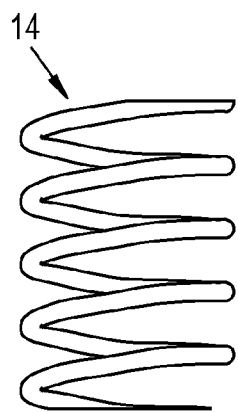
FIG. 20 is a schematic representation of a perspective view of a thread prior to assembly to a screw blank.

D. Making Threads—Manufacturing Options According to the Present Invention
1. Form the threads after the layers have been bonded to create a screw blank (see FIG. 16. FIG. 16 shows the screw blank 10 of the stacked type.)
   a. Machine the threads
   b. Hot form the threads with a mold
2. Form threads in the sheets prior to bonding.
   a. Rolling method: The material will not actually create the complete thread shape until the sheets are formed into the final shape. Continuous or discontinuous threads can be created. Design options for this method include creating raised material that forms the threads (see FIG. 17) or removing material to leave the thread material (see FIG. 18). The raised material in the first method can be created by way of machining, laser ablation, hot stamping, hot or cold forming, chemical etching, electro-discharge machining and similar methods. The material of the second method can be removed by way of machining, laser cutting, stamping, etching, punching, electro-discharge machining, water jet cutting, electron beam machining or other means. FIG. 17 shows a sheet 10 according to the present invention having raised threads 14 formed prior to rolling. FIG. 17 shows raised material to form threads 14. The bottom portion of FIG. 17 (below the broken lines) shows a top view of the sheet 10 prior to rolling. The top portion of FIG. 17 (above the broken lines) shows a side view (more precisely, an edge view) of the sheet 10 prior to rolling. The threads of the bottom portion and top portion of FIG. 17 align with one another per the broken lines, which show the correspondence between the bottom and top portions of FIG. 17. FIG. 18 shows a sheet 10 showing threads 14 formed by material removal prior to rolling. In FIG. 18, D is screw major diameter, t is sheet thickness, and p is screw pitch. FIG. 18 shows a vertical tab T and a horizontal tab T (as oriented on the drawing page), one or both of which may be removable. Porous region is labeled as 12, the circles showing pores. An open area (no material) is labeled as A. The area labeled as B shows a thread region which may be solid or porous or may gradually change from solid to porous starting at the tab and moving inward to the porous region 12. The sheet 10 may be rolled and bonded to make screw 10.
   b. Stacking method: Continuous or discontinuous threads can also be created by this method. The 'ears' of material in each layer 17 form the threads 14 when the layers are stacked (see FIG. 19). These can be created by way of machining, hot stamping, hot or cold forming, dies/punches, chemical etching, electro-discharge machining and similar methods. FIG. 19 shows preformed threads 14 in one layer 17 of a stacked part. Stated another way, FIG. 19 shows a sheet showing threads 14 formed prior to stacking.
3. Add separate threads—Threads can be formed separately and attached to the screw blank. Separate threads can look like 14 in FIG. 20. The material for these threads can include: biocompatible polymers, reinforced biocompatible polymers and/or biocompatible metals. The attachment ways for these threads include:
a. Mechanical attachment—press/interference fit, tabs.
b. Overmolding—mold the solid, porous, or reinforced polymer screw inside of the solid threads or mold the porous, solid or reinforced polymer threads onto the already formed screw.
c. Adhesive or solvent bonding.

E. Cannulation—Manufacturing Options According to the Present Invention

Figure 21:
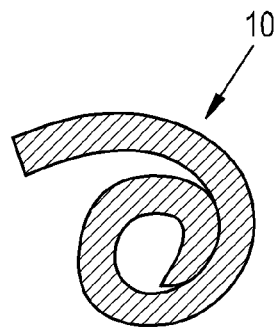
FIG. 21 is a schematic representation of an end view of a screw according to the present invention.

With any of the manufacturing methods, screws can be created with or without a cannula.
1. Cannulated.
   a. Rolling method. In this method, it can be desirable to wind the material around a mandrel that is at the center of the screw, running along its axis. This mandrel can be removed to leave an open cannula (see FIG. 21). FIG. 21 shows a screw 10 with an open cannula after the mandrel is removed during the rolling method.
   b. Layered method. A center hole at the axis of each layer is created to form the cannula when they are stacked together.
2. Non-cannulated.
   a. Rolled method.
      i. The sheet can also be bonded to the mandrel, with the mandrel forming a portion of the implant. This mandrel can be solid or porous and of any implantable material such as PEEK or titanium.
      ii. In addition, the material can be formed around a removable mandrel, creating a cannula. This cannula can be then be filled with a biocompatible material that is attached/bonded to the screw.
   b. Layered method. The layers that are stacked to create the screw can have solid material in place of the holes that would create the cannula. Alternately, they can have cut-outs creating the cannula and this cannula can be filled with a biocompatible material that is attached/bonded to the screw.

Figure 22:
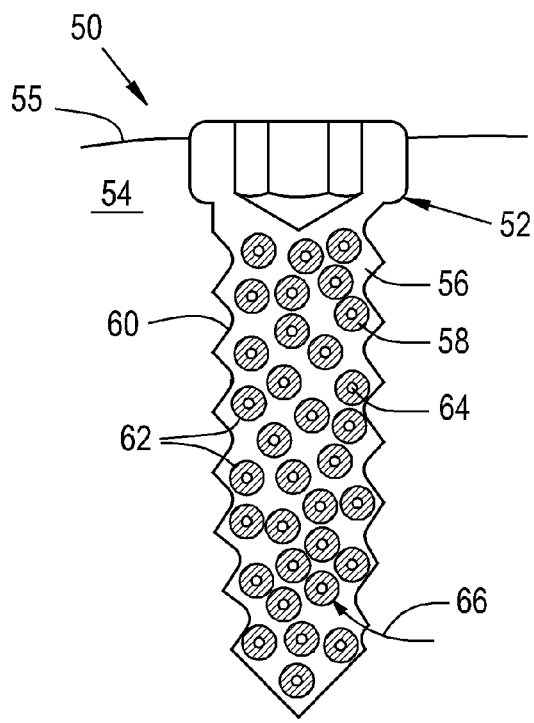
FIG. 22 is a schematic representation of a sectional view of a screw according to the present invention.

Referring now to FIG. 22, there is shown an orthopaedic implant system 50 which includes an orthopaedic implant 52 implantable at a selected location within a corporeal body 54. Implant 52 includes a first structural material 56 and a second structural material 58. First structural material 56 is non-resorbable relative to corporeal body 54 and is different relative to second structural material 58. Stated another way, implant 52 is made of dissimilar materials, first and second structural materials 56 and 58 being dissimilar relative to one another. Implant 52 can be made of additional structural materials as well. Implant 52 is an internal fixation device.

"Structural material" refers to material forming part of the structure of the device. In other words, a therapeutic agent would not be a structural material as used herein. A corporeal body herein means the physical body of a human being or of an animal (i.e., a veterinary patient). Thus, a corporeal body is one of flesh and bones. The corporeal body can be alive or dead. The corporeal body can also be referred to as a patient body herein, which includes both human and veterinary "patients", alive or dead. "Therapeutic agent" is a general term and includes, but is not limited to, pharmaceuticals and biologics (i.e., biological matter). Therapeutic agents can be variously referred to herein, without limitation, as drugs, pharmaceuticals, medicinal agents, or biologics. Therapeutic agents can be formed, for example, as a liquid, a solid, a capsule, or a bead.

An internal fixation device is a device which attaches something to the skeleton (one or more bones) of the corporeal body. An internal fixation device according to the present invention includes, but is not limited to, a bone screw, a bone anchor, a bone tack, a bone graft, or a bone plug. A bone screw, for example, can be used to fix soft tissue (i.e., muscles, ligaments) to bone, or to fix bone to bone. An internal fixation device can be implanted within the corporeal body. Such internal fixation devices may include threads for affixation; alternatively, such internal fixation devices may include barbs (rather than threads) to provide the affixation, may have a smooth shaft with blades at the end of the shaft (the barbs providing the affixation), or may form a press fit with, for example, bone. These examples of the device and the usages of the device are provided by way of example and not by way of limitation.

FIG. 22 shows an orthopaedic bone screw 52 according to the present invention. Screw 52 includes a body 60 made of first structural material 56. Body 60 defines a plurality of pores 62 such that screw 52 is a porous screw. Second structural material 58 fills pores 62. Second structural material 58 can be resorbable relative to corporeal body 54. Alternatively, second structural material 58 can melt away in corporeal body 54. Second structural material 58 can encapsulate or otherwise carry at least one therapeutic agent 64. After implant is implanted in corporeal body 54, second structural material 58, after a predetermined period of time, is configured for melting away in corporeal body 54 and/or resorbing relative to corporeal body 54. Second structural material 58 is configured for releasing said at least one therapeutic agent 64 into corporeal body 54 as said second structural material 58 melts and/or resorbs relative to corporeal body 54. Body 60 is configured for receiving bone and/or soft tissue ingrowth (shown by arrow 66) therein as second structural material 58 melts and/or resorbs relative to corporeal body 54. Thus, in use, screw 52 is implanted in bone 55 of corporeal body 54. After a predetermined period of time, second structural material 58 melts away in corporeal body 54 and/or is resorbed relative to corporeal body 54. First structural material 56 remains implanted in body 54, since material 56 is not resorbable relative to corporeal body 54. Therapeutic agent(s) 64 can thereby be released into corporeal body 54. If second structural material 58 is meltable in corporeal body 54, second structural material 58 has a lower melting point than first structural material 56. Further, glycerine can be used as second structural material 58; glycerine would not resorb relative to corporeal body 54. Glycerine can be injection molded (or a similar process can be used) to form, in part, screw 52.

Figure 23:
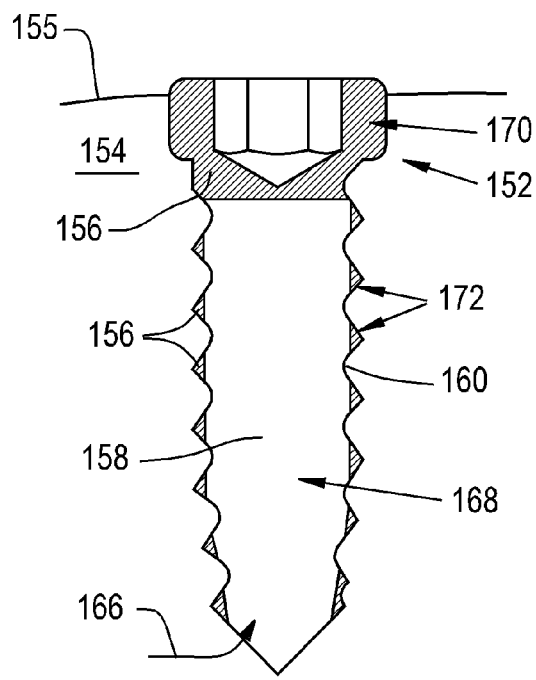
FIG. 23 is a schematic representation of a sectional view of a screw according to the present invention.

FIG. 23 shows an orthopaedic bone screw 152 according to the present invention. Structural features in FIG. 23 corresponding to similar features in FIG. 22 have reference characters raised by multiples of 100. FIG. 23 shows screw 152 implanted in bone 155 of corporeal body 154. Screw 152 includes a core 168, a head 170 attached to core 168, and a plurality of threads 172 about core 168 that are affixed to core 168. Core 168 is made of second structural material 158. Head 170 is made of first structural material 156. Threads 172 (or at least the tips of threads) include first structural material 156 or another structural material which is non-resorbable relative to corporeal body 154. Second structural material 158 (1) has a lower melting point than first structural material 156, (2) is softer than first structural material 156 but not resorbable or meltable in corporeal body 154, and/or (3) is resorbable relative to corporeal body 154.

Second structural material 156 may have a lower melting point than first structural material 156 but not be meltable within corporeal body 154. In this case, having a second structural material 158 which has a lower melting point than first structural material 156 is helpful during the manufacturing process relative to screw 152. Such a second structural material 158 can be injection molded (or a similar process can be used) into and/or relative to the higher melting temperature first structural material 156 to create the final product (i.e., screw 152). This permits the making of unique internal fixation devices, such as unique bone screws. Further, as indicated above, second structural material 156 may indeed be such that it can melt away in corporeal body 154. In use, if core 168 is designed to melt away or resorb relative to corporeal body 154, then only threads 172 and head 170 remain after such melting or resorbing.

Further, when second structural material 158 is softer than first structural material 156 but not resorbable or meltable relative to corporeal body 154, second structural material 158 is configured for facilitating selectively cutting through orthopaedic implant 152 after orthopaedic implant 152 has been implanted in corporeal body 154.

Figure 24:
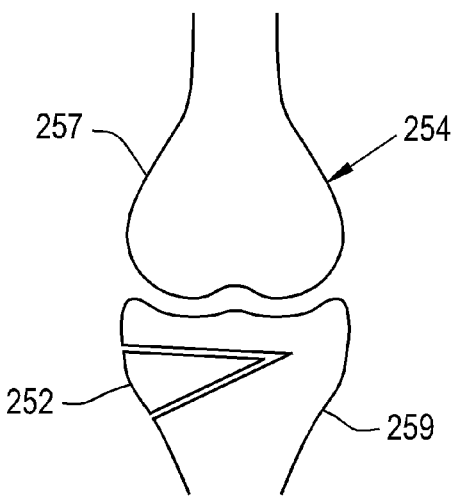
FIG. 24 is a schematic representation of a view of a wedge implant according to the present invention implanted in a corporeal body.
Figure 25:
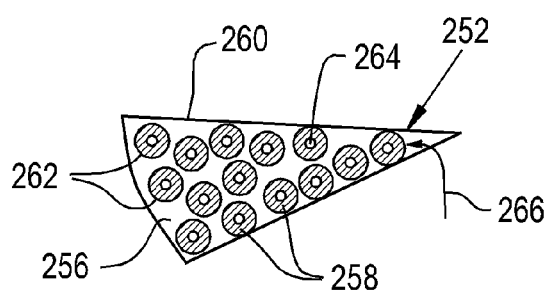
FIG. 25 is a schematic representation of a view of the wedge implant of FIG. 24.

FIGS. 24 and 25 show an orthopaedic augmentation device, such as a bone wedge 252, according to the present invention. Structural features in FIGS. 24-25 corresponding to similar features in FIGS. 22 and/or 23 have reference characters raised by multiples of 100. FIG. 24 shows a knee joint with the femur 257 and the tibia 259 and wedge 252 implanted in the tibia 259. FIG. 24 shows wedge 252 without pores 262 for simplicity and to avoid confusion; it is understood that wedge 252 in FIG. 24 indeed includes pores 262, as shown in FIG. 25. FIG. 25 shows wedge implant 252 with pores 262. After the surgeon performs a tibial osteotomy, wedge 252 can be implanted in the open space in the tibia 259. Wedge 252 includes a body 260 made of first structural material 256. Body 260 defines a plurality of pores 262 such that wedge 252 is a porous wedge. Second structural material 258 fills pores 262. Second structural material 258 can be resorbable relative to corporeal body 254. Alternatively, second structural material 258 can melt away in corporeal body 254. Second structural material 258 can encapsulate or otherwise carry at least one therapeutic agent 264. After implant 252 is implanted in corporeal body 254, second structural material 258, after a predetermined period of time, is configured for melting away in corporeal body 254 and/or resorbing relative to corporeal body 254. Second structural material 258 is configured for releasing at least one therapeutic agent 264 into corporeal body 254 as said second structural material 258 melts and/or resorbs relative to corporeal body 254. Body 260 is configured for receiving bone and/or soft tissue ingrowth 266 therein as second structural material 258 melts and/or resorbs relative to corporeal body 254. Thus, in use, wedge 252 is implanted in tibia 259 of corporeal body 254. After a predetermined period of time, second structural material 258 melts away in corporeal body 254 and/or is resorbed relative to corporeal body 254. First structural material 256 remains implanted in body 260, since material is not resorbable relative to corporeal body 254. Therapeutic agent(s) 264 can thereby be released into corporeal body 254.

Figure 26:
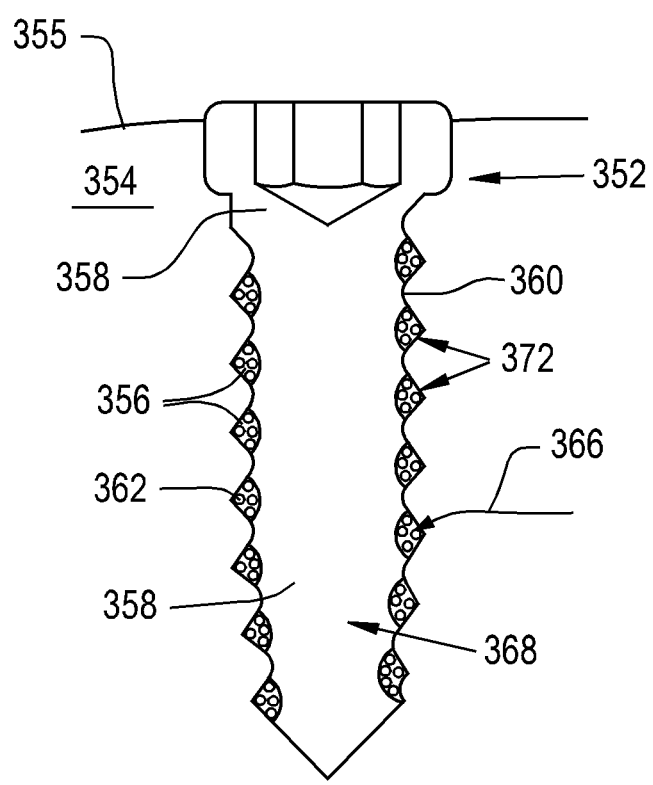
FIG. 26 is a schematic representation of a sectional view of a screw according to the present invention.

FIG. 26 shows an orthopaedic bone screw 352 according to the present invention. Structural features in FIG. 26 corresponding to similar features in FIGS. 22, 23, 24, and/or 25 have reference characters raised by multiples of 100. FIG. 26 shows screw 352 implanted in bone 355 of corporeal body 354. Screw 352 includes a core 368 and a plurality of threads 372 about core 368. Core 368 is made of second structural material 358. Threads 372 are made of first structural material 356. Threads 372 (or at least the tips of the threads 372) include a plurality of pores 362 which are configured for receiving bone and/or soft tissue ingrowth 366 therein. Stated another way, the porous thread tips of threads 372 serve to encourage rapid bone and/or tissue ingrowth and thereby provide a more stable construct when implanted in corporeal body 354. Second structural material 358 (1) has a lower melting point than first structural material 356, (2) is softer than first structural material 356 but not resorbable or meltable in corporeal body 354, and/or (3) is resorbable relative to corporeal body 356. The purpose and behavior of second structural material 358 with regard to these three alternatives are described above and apply to screw 352 as well.

With regard to the internal fixation device of the present invention, the first structural material can include stainless steel, titanium, a titanium alloy, a cobalt chrome alloy, polyetheretherketone, and/or polyethylene. These examples of the first structural material are provided by way of example and not by way of limitation.

In one embodiment of the internal fixation device of the present invention, the first structural material can be polyetheretherketone, the second structural material being softer than the first structural material. The second structural material can be polyethylene. These examples of the first and second structural materials are provided by way of example and not by way of limitation.

In another embodiment of the internal fixation device of the present invention, the first structural material can be titanium, the second structural material being softer than the first structural material. The second structural material can be polyetheretherketone. These examples of the first and second structural materials are provided by way of example and not by way of limitation.

In another embodiment of the internal fixation device of the present invention, the first structural material can be titanium, the second structural material having a lower melting point than the first structural material. The second structural material can be polyetheretherketone or polyethylene. These examples of the first and second structural materials are provided by way of example and not by way of limitation.

In another embodiment of the internal fixation device of the present invention, the first structural material can be polyetheretherketone, the second structural material having a lower melting point than the first structural material. The second structural material can be polyethylene. These examples of the first and second structural materials are provided by way of example and not by way of limitation.

The present invention thus provides orthopaedic screws and other implants with multiple materials and/or therapeutic delivery capability. More specifically, the present invention provides the following:

1) The combination of a porous or hollow screw or other medical implant with other dissimilar material (this combination hereinafter referred to as "the device of Item (1)").
   a. The device noted in Item (1) with the ability to deliver therapeutic agents (hereinafter "the device of Item (1a)").
   b. The device of Item (1) with the ability to allow the body's building blocks (stem cells, etc.) to flow into the device to promote tissue healing and in-growth.
   c. The device of Item (1) and/or the device of Item (1a) with the ability to allow the in-growth of tissue into non-resorbable portions of the screw (hereinafter "the device of Item (1c)").
   d. The device of Item (1) and/or the device of Item (1c) with the ability to allow the in-growth of tissue into the space occupied by the resorbable material (hereinafter "the device of Item (1d)").
   e. The device of Item (1) and/or the device of Item (1 d) with the ability to reduce the amount of residual (over a period of time the resorbable material will dissolve) material in the body while structural/strengthening member remains behind.
2) Porous screw (hereinafter "the device of Item (2)").
   a. The device of Item (2) with the ability to deliver therapeutic agents (hereinafter "the device of Item (2a)").
   b. The device of Item (2) with the ability to allow the body's building blocks (stem cells, etc.) to flow into the device to promote tissue healing and in-growth.
   c. The device of Item (2) and/or the device of Item (2a) with the ability to allow the in-growth of tissue into the screw.
3) Specific Design Combinations, such as:
   a. PEEK (polyetheretherketone) with Resorbable material
   b. Titanium with Resorbable material
   c. Any other combinations of metals and plastics and/or resorbables.
4) Other implants having combinations of materials. Examples of these implants include, but are not limited to, the following: bone augment or wedge, tacks, bone plug, and fusion devices.
5) The manufacturing method can include manufacturing steps disclosed above. The present invention thus includes these manufacturing steps along with the added step of molding a second structural material within the screw, the second structural material having a lower melting point than the first structural material, being softer than the first structural material (but not resorbable or meltable in the corporeal body), and/or being resorbable in the corporeal body.

Unless specifically indicated otherwise, the meaning of "tissue", as used herein, refers to bone and/or soft tissues.

The present invention thus generally provides implants including multiple materials. Examples of such implants include, but are not limited to, the following: screws, bone augmentations or wedges, tacks, anchors, bone plugs, and fusion devices. These devices, according to the present invention, include a plurality of materials, with at least one material being non-resorbable. The devices of the present invention are configured for attaching various soft tissues to bone, and/or for attaching bone to bone, and/or for delivering therapeutic agents (for example biologics or drugs) to soft tissue and/or bone, and/or for promoting the fusion of one or more bone pieces or bones.

As discussed above, the devices include at least one non-resorbable material (material A—that is, the first structural material as described above). Examples of non-resorbable, implantable materials include, but are not limited to, stainless steel, titanium, titanium alloy, cobalt chrome alloys, PEEK (Poly(etheretherketone)), and polyethylene. This material can be in any form such as solid, porous, or laminate. The device includes at least one additional material (material B—that is, the second structural material as described above). Material B can be a non-resorbable material (for example any of those listed above), can be a material which resorbs in the corporeal body, can have a lower melting point than the Material A, and/or can be softer than the Material A (but not resorbable or meltable in the corporeal body). Examples of resorbable, implantable materials include, but are not limited to, PLA (Poly(lactic acid)), PGA (poly(glycolic acid)), and PLLA (Poly-L-Lactic-acid). The device can include additional resorbable and non-resorbable materials.

The devices of the present invention provide the following:

Minimize the amount of material and/or hard material (such as metal) that remains in the body in the long term (beyond the time typical resorbable materials resorb).
Provide an option to deliver therapeutics to surrounding tissue.
Provide regions for tissue ingrowth.

The following discusses each of these three in more detail.

1. Minimize long-term material and/or hard material (such as metal). Because one individual may need to undergo multiple surgeries on a given joint, it is desirable to minimize the amount of material and/or hard material remaining in the body long-term. The more material and/or hard material that remains, the greater the difficulty it can cause in future surgeries. For example, if a solid metal or PEEK screw is left in a femoral condyle and a subsequent total knee replacement (TKR) is required, that screw may interfere with the placement of the TKR implants. If the screw does interfere, it can be removed or cut through. Minimizing the long term material and/or hard material that remains can allow the surgeon to more easily cut through the screw and place the subsequent implant.
   a. An implant with one or more resorbable and/or meltable portions and one or more non-resorbable portions provides a way of minimizing the long-term material. One example of this type of implant is a screw including a porous scaffold made from non-resorbable material with resorbable and/or meltable material filling some or all pores (see FIG. 22). For instance, a porous PEEK screw can be filled with PLLA. Another example provides a screw including non-resorbable thread tips and screw head, while the remainder of the screw includes a soft polymer material such as polyethylene (see FIG. 23). A third example is that of a porous tibial bone replacement wedge (see FIGS. 24 and 25). Resorbable material can be used to fill the pores in a non-resorbable porous material to provide increased strength while the surrounding bone is healing in addition to the benefits discussed in (2) and (3) below.

One role of the resorbable and/or meltable material (the second structural material), as well as the soft material, is to provide additional strength and support (beyond that of the non-resorbable material(s) alone) during insertion and in first weeks after surgery, as the tissue heals. For example, in ACL reattachment, the screw that attaches the ACL to the bone must carry less and less load as the ACL heals and reattaches to the bone. Thus, as time passes lower strength and stiffness is required than during implantation and immediately after the surgery. The resorbable and/or meltable material can be designed to resorb and/or melt at a rate such that sufficient material properties are maintained through the time required for tissue healing.

One role of the non-resorbable material (the first structural material) is to provide additional strength and support (beyond that of the resorbable and/or meltable materials(s) alone) during insertion. For example, in ACL reattachment, the screw that attaches the ACL to the bone can fracture during insertion causing surgical delays. Addition of the non-resorbable material can prevent insertion failure by increasing the overall strength of the device.

2. Delivery of therapeutic agents. The resorbable and/or meltable material (the second structural material) can also be used to carry therapeutic agents to the tissue surrounding the implant. Examples of the goal of these agents include, but are not limited to, encouraging tissue healing and ingrowth, preventing and/or treating infection, preventing and/or treating osteoarthritis, and/or reducing pain. Some types of agents that can be delivered are, but are not limited to, drugs and/or biologic agents (cells, proteins, growth factors). The resorbtion and/or meltable rate of the resorbable and/or meltable material and release rate of the therapeutic agents can be customized to a given application.

3. Porous to allow for tissue ingrowth. Porous regions can allow for tissue ingrowth, providing a potentially more stable device than without the regions of ingrowth. The entire device or specific regions (such as the thread tips—see FIG. 26) can be porous. The device in FIG. 26 can be manufactured by creating the porous threads (some specific ways of doing so are disclosed above) and then insert molding the resorbable and/or meltable core.

The concept of a porous screw is disclosed above.

The present invention thus provides for a porous screw with resorbable, meltable, and/or soft materials to provide increased strength, allow for design options that would leave less residual and/or hard material, provide another vehicle for the delivery of therapeutic agents, and provide a way to manufacture internal fixation devices having one material that has a lower melting point than the other material.

The present invention further provides a method for using an orthopaedic implant system 50, the method including the steps of: providing an orthopaedic implant 52 including a first structural material 56 and a second structural material 58, the first structural material 56 being non-resorbable relative to a corporeal body 54 and being different relative to the second structural material 58, the implant 52 being an internal fixation device; and implanting the orthopaedic implant 52 at a selected location within the corporeal body 54. The internal fixation device is a bone screw 52, a bone anchor, or a bone tack.

The second structural material 158, 358 can be softer than the first structural material 156, 356. The method further includes the second structural material 158, 358 facilitating selectively cutting through the orthopaedic implant 152, 352 after the orthopaedic implant 152, 352 has been implanted in the corporeal body 154, 354.

The method further includes melting the second structural material 58, 158, 258, 358, the second structural material 58, 158, 258, 358 having a lower melting point than said first structural material 56, 156, 256, 356.

The method further includes carrying at least one therapeutic agent 64, 264 by the second structural material 58, 258, and releasing the at least one therapeutic agent 64, 264 by the second structural material 58, 258 into the corporeal body 54, 254 as the second structural material 58, 258 melts.

The implant includes a body 60, 160, 260, 360 made of the first structural material 56, 156, 256, 356, the body 60, 160, 260, 360 receiving at least one of bone and soft tissue ingrowth 66, 166, 266, 366 therein as the second structural material 58, 158, 258, 358 melts.

The orthopaedic implant is a bone screw 152 which includes a core 168, a head 170 attached to the core 168, and a plurality of threads 172 about the core 168, the core 168 being made of the second structural material 158, the head 170 being made of the first structural material 156, the plurality of threads 172 including the first structural material 156 or another structural material which is non-resorbable relative to the corporeal body 154, the second structural material 158 (1) melting, the second structural material 158 having a lower melting point than the first structural material 156, and/or (2) being softer than the first structural material 156.

The orthopaedic implant is a bone screw 352 which includes a core 368 and a plurality of threads 372 about the core 368, the core 368 being made of the second structural material 358, the plurality of threads 372 being made of the first structural material 356, the plurality of threads 372 including a plurality of pores 362 which receive bone and/or soft tissue ingrowth 366 therein, the second structural material 358 (1) melting, the second structural material 358 having a lower melting point than the first structural material 356, and/or (2) being softer than the first structural material 356.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant system, comprising:
an orthopaedic implant implantable at a selected location within a corporeal body, said implant including a first structural material and a second structural material, said first structural material being non-resorbable relative to said corporeal body and being different relative to said second structural material, said second structural material being resorbable relative to said corporeal body, said orthopaedic implant being an internal fixation device, said orthopaedic implant including a core and a plurality of threads about said core, said core being made of said second structural material, said plurality of threads being made of said first structural material, said orthopaedic implant having no other threads than said plurality of threads, said plurality of threads including a first longitudinal end and an opposing second longitudinal end, said core extending from said first longitudinal end to said second longitudinal end, said plurality of threads being directly affixed to said second structural material of said core, wherein said first structural material is polyetheretherketone and said second structural material at least one of has a lower melting point than said first structural material and is softer than said first structural material.

2. The orthopaedic implant system of claim 1, wherein said internal fixation device is one of a bone screw and a bone anchor.

3. The orthopaedic implant system of claim 2, wherein said second structural material is softer than said first structural material.

4. The orthopaedic implant system of claim 3, wherein said second structural material is configured for facilitating cutting through at least a portion of said orthopaedic implant after said orthopaedic implant has been implanted in said corporeal body.

5. The orthopaedic implant system of claim 2, wherein said second structural material has a lower melting point than said first structural material.

6. The orthopaedic implant system of claim 2, further including at least one therapeutic agent carried by said second structural material, said second structural material being configured for releasing said at least one therapeutic agent into said corporeal body as said second structural material melts.

7. The orthopaedic implant system of claim 2, wherein said implant includes a body made of said first structural material, said body being configured for receiving at least one of bone and soft tissue ingrowth therein as said second structural material melts.

8. The orthopaedic implant system of claim 2, wherein said orthopaedic implant is a bone screw which includes a head attached to said core, said head being made of said first structural material.

9. The orthopaedic implant system of claim 2, wherein said orthopaedic implant is a bone screw, said plurality of threads including a plurality of pores which are configured for receiving at least one of bone and soft tissue ingrowth therein.

10. The orthopaedic implant system of claim 1, wherein said second structural material is a polymer.

11. A method of using an orthopaedic implant system, said method comprising the steps of:
providing an orthopaedic implant including a first structural material and a second structural material, said first structural material being non-resorbable relative to a corporeal body and being different relative to said second structural material, said second structural material being resorbable relative to said corporeal body, said orthopaedic implant being an internal fixation device, said orthopaedic implant including a core and a plurality of threads about said core, said core being made of said second structural material, said plurality of threads being made of said first structural material, said orthopaedic implant having no other threads than said plurality of threads, said plurality of threads including a first longitudinal end and an opposing second longitudinal end, said core extending from said first longitudinal end to said second longitudinal end, said plurality of threads being directly affixed to said second structural material of said core, wherein said first structural material is polyetheretherketone and said second structural material at least one of has a lower melting point than said first structural material and is softer than said first structural material; and
implanting said orthopaedic implant at a selected location within said corporeal body.

12. The method of claim 11, wherein said internal fixation device is one of a bone screw and a bone anchor.

13. The method of claim 12, wherein said second structural material is softer than said first structural material.

14. The method of claim 13, further including said second structural material facilitating cutting through at least a portion of said orthopaedic implant after said orthopaedic implant has been implanted in said corporeal body.

15. The method of claim 12, further including melting said second structural material, said second structural material having a lower melting point than said first structural material.

16. The method of claim 12, further including carrying at least one therapeutic agent by said second structural material, and releasing said at least one therapeutic agent by said second structural material into said corporeal body as said second structural material melts.

17. The method of claim 12, wherein said implant includes a body made of said first structural material, said body receiving at least one of bone and soft tissue ingrowth therein as said second structural material melts.

18. The method of claim 12, wherein said orthopaedic implant is a bone screw which includes a head attached to said core, said head being made of said first structural material.

19. The method of claim 12, wherein said orthopaedic implant is a bone screw, said plurality of threads including a plurality of pores which receive at least one of bone and soft tissue ingrowth therein.

20. The method of claim 12, wherein said second structural material is a polymer.

* * * * *